(12) United States Patent
Ben-David

(10) Patent No.: US 7,885,709 B2
(45) Date of Patent: Feb. 8, 2011

(54) NERVE STIMULATION FOR TREATING DISORDERS

(75) Inventor: Tamir Ben-David, Tel Aviv (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 979 days.

(21) Appl. No.: 11/234,877

(22) Filed: Sep. 22, 2005

(65) Prior Publication Data

US 2006/0100668 A1 May 11, 2006

Related U.S. Application Data

(60) Provisional application No. 60/668,275, filed on Apr. 4, 2005, provisional application No. 60/612,428, filed on Sep. 23, 2004.

(51) Int. Cl.
*A61N 1/36* (2006.01)
(52) U.S. Cl. .......................................................... 607/2
(58) Field of Classification Search ....................... 607/2
See application file for complete search history.

(56) References Cited

U.S. PATENT DOCUMENTS

| | | |
|---|---|---|
| 3,411,507 A | 11/1968 | Wingrove |
| 4,019,518 A | 4/1977 | Maurer et al. |
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | van den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |

(Continued)

FOREIGN PATENT DOCUMENTS

EP 0 688 577 A1 12/1995

(Continued)

OTHER PUBLICATIONS

Cummings, J.E., et al., "Preservation of the anterior fat pad paradoxically decreases the incidence of postoperative atrial fibrillation in humans", J. Am. Coll. Cardiol., 2001, vol. 43, No. 6, pp. 994-1000.

(Continued)

*Primary Examiner*—Michael Kahelin
(74) *Attorney, Agent, or Firm*—John P. White; Cooper & Dunham LLP

(57) ABSTRACT

This invention provides a method for treating a condition of a subject, comprising identifying the subject as suffering from heart failure; treating the heart failure by applying a stimulating current to parasympathetic nervous tissue of the subject, and configuring the stimulating current to change a level of protein expression of at least one NO synthase of the subject selected from the group consisting of: NOS-1, NOS-2, and NOS-3; and thereafter, measuring the level of the protein expression of at least one NO synthase, and evaluating an effectiveness of the current application by assessing at least one change in the level of the protein expression of at least one NO synthase.

16 Claims, 13 Drawing Sheets

U.S. PATENT DOCUMENTS

| | | |
|---|---|---|
| 4,632,116 A | 12/1986 | Rosen |
| 4,649,936 A | 3/1987 | Ungar |
| 4,663,102 A | 5/1987 | Brenman et al. |
| 4,702,254 A | 10/1987 | Zabara |
| 4,739,764 A | 4/1988 | Lue |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,058,599 A | 10/1991 | Andersen et al. |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,224,491 A | 7/1993 | Mehra |
| 5,243,980 A | 9/1993 | Mehra |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry, Jr. |
| 5,356,425 A | 10/1994 | Bardy |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,487,756 A | 1/1996 | Kallesoe et al. |
| 5,507,784 A | 4/1996 | Hill et al. |
| 5,522,854 A | 6/1996 | Ideker et al. |
| 5,540,730 A | 7/1996 | Terry, Jr. |
| 5,540,734 A | 7/1996 | Zabara |
| 5,562,718 A | 10/1996 | Palermo |
| 5,571,150 A | 11/1996 | Wernicke |
| 5,575,766 A * | 11/1996 | Swartz et al. ............... 604/508 |
| 5,578,061 A | 11/1996 | Stroetmann et al. |
| 5,615,684 A | 4/1997 | Hagel et al. |
| 5,634,462 A | 6/1997 | Tyler |
| 5,645,570 A | 7/1997 | Corbucci et al. |
| 5,658,318 A | 8/1997 | Stroetmann et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,824,027 A | 10/1998 | Hoffer |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 6,006,134 A | 12/1999 | Hill et al. |
| 6,026,326 A | 2/2000 | Bardy |
| 6,058,328 A | 5/2000 | Levine et al. |
| 6,058,331 A | 5/2000 | King et al. |
| 6,066,163 A | 5/2000 | John |
| 6,073,048 A | 6/2000 | Kieval et al. |
| 6,086,525 A | 7/2000 | Davey et al. |
| 6,091,922 A | 7/2000 | Bisaiji |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,956 A | 8/2000 | Naritoku et al. |
| 6,104,960 A | 8/2000 | Duysens et al. |
| 6,119,516 A | 9/2000 | Hock |
| H1905 H | 10/2000 | Hill |
| 6,134,470 A | 10/2000 | Hartlaub |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 | 7/2001 | Hill |
| 6,272,377 B1 | 8/2001 | Sweeney et al. |
| 6,292,695 B1 | 9/2001 | Webster, Jr. et al. |
| 6,319,241 B1 | 11/2001 | King |
| 6,341,236 B1 | 1/2002 | Osorio |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,511,500 B1 | 1/2003 | Rahme |
| 6,522,926 B1 | 2/2003 | Kieval et al. |
| 6,542,774 B2 | 4/2003 | Hill et al. |
| 6,564,096 B2 | 5/2003 | Mest |
| 6,571,122 B2 | 5/2003 | Schroeppel et al. |
| 6,587,727 B2 | 7/2003 | Osorio et al. |
| 6,600,956 B2 | 7/2003 | Maschino |
| 6,605,447 B2 * | 8/2003 | Weiss et al. ................... 435/37 |
| 6,610,713 B2 | 8/2003 | Tracey |
| 6,622,041 B2 | 9/2003 | Terry, Jr. et al. |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen et al. |
| 6,690,971 B2 | 2/2004 | Schauerte et al. |
| RE38,705 E | 2/2005 | Hill et al. |
| 6,865,416 B2 | 3/2005 | Dev et al. |
| 6,885,888 B2 | 4/2005 | Rezai et al. |
| 6,895,280 B2 | 5/2005 | Meadows et al. |
| 6,907,293 B2 | 6/2005 | Grill et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,509,166 B2 | 3/2009 | Libbus |
| 7,623,926 B2 | 11/2009 | Rossing et al. |
| 2002/0035335 A1 | 3/2002 | Schauerte |
| 2002/0107553 A1 | 8/2002 | Hill et al. |
| 2002/0120304 A1 | 8/2002 | Mest |
| 2003/0018367 A1 | 1/2003 | DiLorenzo |
| 2003/0027794 A1 * | 2/2003 | Arnaiz et al. ................. 514/79 |
| 2003/0040774 A1 | 2/2003 | Terry et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0100924 A1 | 5/2003 | Foreman et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |

| | | |
|---|---|---|
| 2003/0236558 A1 | 12/2003 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0193231 A1 | 9/2004 | David et al. |
| 2004/0199210 A1 | 10/2004 | Shelchuk |
| 2004/0215087 A1* | 10/2004 | Genero et al. ............... 600/508 |
| 2004/0215289 A1 | 10/2004 | Fukui |
| 2004/0243182 A1 | 12/2004 | Cohen et al. |
| 2004/0249416 A1 | 12/2004 | Yun et al. |
| 2004/0254612 A1 | 12/2004 | Ezra et al. |
| 2005/0065553 A1 | 3/2005 | Ben Ezra et al. |
| 2005/0131467 A1 | 6/2005 | Boveja |
| 2005/0187584 A1 | 8/2005 | Denker et al. |
| 2005/0197675 A1 | 9/2005 | David et al. |
| 2005/0222644 A1 | 10/2005 | Killian et al. |
| 2005/0267542 A1 | 12/2005 | David et al. |
| 2006/0015153 A1 | 1/2006 | Gliner et al. |
| 2006/0047325 A1 | 3/2006 | Thimineur et al. |
| 2006/0052831 A1 | 3/2006 | Fukui |
| 2006/0064140 A1 | 3/2006 | Whitehurst et al. |
| 2006/0074450 A1 | 4/2006 | Boveja et al. |
| 2006/0129205 A1 | 6/2006 | Boveja et al. |
| 2006/0149337 A1 | 7/2006 | John |
| 2006/0167498 A1 | 7/2006 | DiLorenzo |
| 2008/0228238 A1* | 9/2008 | Libbus ........................ 607/44 |

FOREIGN PATENT DOCUMENTS

| | | |
|---|---|---|
| EP | 0831954 | 4/1998 |
| WO | WO-01/10375 A2 | 2/2001 |
| WO | WO-01/10432 | 2/2001 |
| WO | WO-01/26729 | 4/2001 |
| WO | WO-02/085448 A1 | 10/2002 |
| WO | WO 03/099377 | 12/2003 |
| WO | WO 2004/103455 | 12/2004 |
| WO | WO 2004/110549 | 12/2004 |
| WO | WO 2004/110550 | 12/2004 |
| WO | WO 2006/102370 A2 | 9/2006 |

OTHER PUBLICATIONS

Kwan, Herman, et al., "Cardiovascular adverse drug reactions druing initiation of antiarrhythmic therapy for atrial fibrillation", Can. J. Hosp. Pharm., 2001, vol. 54, pp. 10-14.
Hjalmarson, Ake, "Prevention of sudden cardiac death with beta blockers", Clin. Cardiol., 1999, vol. 22, Supoplement V, pp. V-11-V-15.
Bilgutay, Aydin M., et al., "Vagal tuning a new concept in the treatment of supraventricular arrhythmias, angina pectoris and heart failure", J. Thoracic Cardiovasc. Surg., vol. 56, No. 1, pp. 71-82, Jul. 1968.
Manfredi, M., "Differential Block of conduction of larger fibers in peripheral nerve by direct current", Arch. Ital. Biol., vol. 108, pp. 52-71, 1970.
Friedrichs, Gregory S., "Experimental models of atrial fibrillation/ flutter", Journal of Pharmacological and Toxoligical Methods, 2000, vol. 43, pp. 117-1123.
Rijkhoff, N.J.M., et al., "Selective Stimulation of Small Diameter Nerve Fibers in a Mixed Bundle", Proceedings of the Annual Project Meeting Sensations/Neuros and Mid Term Review Meeting Neuros, pp. 21-23, Apr. 1999.
Zhang, Y., et al., "Optimal Ventricular Rate Slowing During Atrial Fibrillation by Feedback AV Nodal-Selective Vagal Stimulation", Am. J. Physiol. Heart Circ. Physiol. 282:H1102-H1110, 2002.
Fuster, Valentin, et al., "ACC/AHA/ESC Practice Guidelines", JACC, vol. 38, No. 4, 2001.
Jideus, "Atrial fibrillation after corony artery bypass surgery", Acta Universitatis Upsaliensis, Uppsala 2001.
Li et al., "Promotion of atrial fibrillation by heart failure in dogs", Circulation, Jul. 6, 1999, pp. 87-95.
Carlson MD et al., "Selective stimulation of parasympathetic nerve fibers to the human sinoatrial node," Circuation 85:1311-1317 (1992).
Page PL et al., "Regional distribution of atrial electrical changes induced by stimulation of extracardiac and intracardiac neural elements," J Thorac Cardiovasc Surg. 109(2):377-88 (1995).
Furukawa Y et al., "Differential blocking effects of atropine and gallamine on negative chrontropic and dromotropic responses to vagus stimulation in anesthetized dogs," J Pharmacol Exp. Ther. 251(3):797-802 (1989).
Bluemel KM, "Parasympathetic postganglionic pathways to the sinoatrial node, " J Physiol. 259 (5 Pt 2): H1504-10 (1990).
Bibevski S et al. "Ganglionic Mechanisms Contribute to Diminished Vagal Control in Heart Failure," Circulation 99:2958-2963 (1999).
Garrigue S et al., "Post-ganglionic vagal stimulation of the atrioventricular node reduces ventricular rate during atrial fibrillation,"Pace 21(4), Part II, 878 (1998).
Chen SA et al., "Intracardiac stimulation of human parasympathetic nerve fibers induces negative dromotropic effects: implication with the lesions of radiofrequency catheter ablation, " J Cardiovasc Electrophysiol. 9(3):245-52 (1998).
Cooper et al., "Neural effects on sinus rate and atrial ventricular conduction produced by electrical stimulation from a transvenous electrode catheter in the canine right pulmonary artery" Circ Res vol. 46(1):48-57 (1980).
Waninger MS et al., "Electrophysiological control of ventricular rate during atrial fibrillation," PACE 23:1239-1244 (2000).
Goldberger JJ et al., "New technigue for vagal nerve stimulation," J Neurosci Methods. 91(1-2):1089-14 (1999).
Schaldach M, "New concepts in electrotherapy of the heart", Electrotherapy of the Heart, Springer Verlag Heidelberg, pp. 210-214 (1992).
Office Action issued Apr. 5, 2007 during the prosecution of Applicants' U.S. Appl. No. 10/488,334.
Van den Honert, C. et al., (1979) "Generation of unidirectionally propagated action potentials in a peripheral nerve by brief stimuli," *Science*, vol. 206: 1311-1312.
Akselrod, S. et al., (1981) "Power spectrum analysis of heart rate fluctuation: A quantitative probe of beat-to-beat cardiovascular control," *Science* 213:220-222.
Baratta, R. et al., (1989) "Orderly stimulation of skeletal muscle motor units with tripolar nerve cuff electrode," *IEEE Transactions on Biomedical Engineering* 36(1):836-843.
Billette, J. et al., (1975) "Roles of the AV junction in determining the ventricular response to atrial fibrillation," *Canadian Journal of Physiological Pharmacology* 53(4):575-585.
Borovikova, L. et al., (May 25, 2000) "Vagus nerve stimulation attenuates the systemic inflammatory response to endotoxin," *Nature* 405:458-462.
Chen, S. et al., (1998) "Intracardiac stimulation of human parasympathetic nerve fibers induces negative dromotropic effects: implication with the lesions of radiofrequency catheter ablation," *Journal of Cardiovascular Electrophysiology* 9(3):245-252.
De Ferrari, G. et al, (1991) "Vagal reflexes and survival during acute myocardial ischemia in conscious dogs with healed myocardial infarction," *American Journal of Physiology* 261(1 Pt 2):H63-H69.
Deurloo, K. et al., (1998) "Transverse tripolar stimulation of peripheral nerve: a modeling study of spatial selectivity," *Medical & Biological Engineering & Computing* 36(1):66-74.
Fitzpatrick, D. et al., (1991) "A nerve cuff design for the selective activation and blocking of myelinated nerve fibers," *Annual International Conference. of the IEEE Engineering in Medicine and Biology* 13(2):906-907.
Garrigue, S. et al., (1998) "Post-ganglionic vagal stimulation of the atrioventricular node reduces ventricular rate during atrial fibrillation," PACE 21(4):356 (Part II).
Goodall, E. et al., (1996) "Position-selective activation of peripheral nerve fibers with a cuff electrode," *IEEE Transactions on Biomedical Engineering* 43(8):851-856.

Grill, W. (1997) "Inversion of the current-distance relationship by transient depolarization," *IEEE Transactions on Biomedical Engineering* 44(1):1-9.

Hayashi, H. et al., (1998) "Different effects of class Ic and III antiarrhythmic drugs on vagotonic atrial fibrillation in the canine heart," *Journal of Cardiovascular Pharmacology* 31:101-107.

Higgins, C. et al., S., (1973) "Parasympathetic control of the heart," *Pharmacological. Reviews* 25(1):120-155.

Jideus, L. (2001) "Atrial fibrillation after coronary artery bypass surgery: A study of causes and risk factors," *Acta Universitatis Upsaliensis* pp. 1-56.

Jones, J. et al., (1995) "Heart rate responses to selective stimulation of cardiac vagal C fibres in anaesthetized cats, rats and rabbits", *Journal of Physiology* 489(1):203-214.

Kamath, M. et al., (1992) "Effect of vagal nerve electrostimulation on the power spectrum of heart rate variability in man," PACE vol. 15, *Clinical Electrophysiology* 15:235-243.

Kwan, H. et al., (2001) "Cardiovascular adverse drug reactions during initiation of antiarrhythmic therapy for atrial fibrillation," *Canadian Journal of Hospital Pharmacy* 54(1):10-14.

Li, D. et al., (1999) "Promotion of Atrial Fibrillation by Heart Failure in Dogs: Atrial Remodeling of a Different Sort," *Circulation* 100(1):87-95.

Manfredi, M. (1970) "Differential block of conduction of larger fibers in peripheral nerve by direct current," *Archives Italiennes de Biologie* 108:52-55.

Martin, P. et al., (1983) "Phasic effects of repetitive vagal stimulation on atrial contraction," *Circulation Research* 52(6):657-663.

Morady, F. et al., (1990) "Effects of resting vagal tone on accessory atrioventricular connections," *Circulation* 81(1):86-90.

Mushahwar, V. and Korch, K., (2000) "Muscle recruitment through electrical stimulation of the lumbo-sacral spinal cord," *IEEE Transactions on Rehabilitation Engineering* 8(1):9-22.

Naples, G. et al., (1988) "A spiral nerve cuff electrode for peripheral nerve stimulation," *IEEE Transactions on Biomedical Engineering* 35(11):905-916.

Randall, W. ed., (1977) "Neural Regulation of the Heart", *Oxford University Press*, particularly pp. 100-106.

Rijkhoff, N. et al., (1994)"Acute animal studies on the use of anodal block to reduce urethral resistance in sacral root stimulation," *IEEE Transactions on Rehabilitation Engineering*, 2(2):92-99.

Rijkhoff, N. et al., (1998) "Orderly recruitment of motoneurons in an acute rabbit model," *Proc. of the Annual Conf. of the IEEE Engineering in Medicine and Biology Society* 20(5):2564-2565.

Stramba-Badiale, M. et al, (1991) "Sympathetic-Parasympathetic Interaction and Accentuated Antagonism in Conscious Dogs," *American Journal of Physiology* 260 (2Pt 2):H335-340.

Sweeney, J. et al., (1990) "An asymmetric two electrode cuff for generation of unidirectionally propagated action potentials," *IEEE Transactions on Biomedical Engineering* BME-33(6):541-549.

Sweeney, J. et al., (1986) "A nerve cuff technique for selective excitation of peripheral nerve trunk regions," *IEEE Transactions on Biomedical Engineering*, 37(7):706-715.

Takei, M. et al., (2001)"Vagal stimulation prior to atrial rapid pacing protects the atrium from electrical remodeling in anesthetized dogs," *Japanese Circulation Journal* 65(12):1077-1081.

Tarver, W. et al., (1992)"Clinical experience with a helical bipolar stimulating lead," *Pace* vol. 15, October, Part II 1545-1156.

Tsuboi, M. et al., (2000) "Inotropic, chronotropic, and dromotropic effects mediated via parasympathetic ganglia in the dog heart," *American Journal of Physiology Heart Circulation Physiology* 279:H1201-H1207.

Ungar, I. et al., (1986) "Generation of unidirectionally propagating action potentials using a monopolar electrode cuff," *Annals of Biomedical Engineering* 14:437-450.

Van Den Honert, C. et al., (1981) "A technique for collision block of peripheral nerve: Frequency dependence," *MP-12, IEEE Transactions on Biomedical Engineering* 28:373-378.

Van Den Honert, C. et al., (1979) "Generation of unidirectionally propagated action potentials in a peripheral nerve by brief stimuli," *Science* 206:1311-1312.

Vanoli, E. et al., (1991) "Vagal stimulation and prevention of sudden death in conscious dogs with a healed myocardial infarction," *Circulation Research* 68(5):1471-1481.

Veraart, C. et al., (1993) "Selective control of muscle activation with a multipolar nerve cuff electrode," *IEEE Transactions on Biomedical Engineering* 40(7):640-653.

Wallick, D. et al., (2001) "Selective AV nodal vagal stimulation improves hemodynamics during acute atrial fibrillation in dogs," *American Journal of Physiology Heart Circulation Physiology* 281:H1490-H1497.

Wang, H. et al., (2003) "Nicotinic acetylcholine receptor alpha-7 subunit is an essential regulator of inflammation," *Nature* 421:384-388.

Waninger, M. et al., (2000) "Electrophysiological control of ventricular rate during atrial fibrillation," *PACE* 23:1239-1244.

Wijffels, M. et al., (1995) "Atrial fibrillation begets atrial fibrillation," *Circulation* 92:1954-1968.

Nov. 1, 2007 Office Action issued by the U.S. Patent and Trademark Office in connection with U.S. Appl. No. 10/205,475.

Jones, J. F. X. et al., (1995) "Heart Rate Responses to Selective Stimulation of Cardiac Vagal C Fibres in Anaesthetized Cats, Rats and Rabbits," *Journal of Physiology*, 489(1): 203-214.

Jones, J.F.X. et al., (1998) "Activity of C Fibre Cardiac Vagal Efferents in Anaesthetized Cats and Rats," Journal of Physiology, 507(3) 869-880.

Office Action, issued Apr. 1, 2009, in connection with U.S. Appl. No. 11/359,266, filed Feb. 21, 2006.

* cited by examiner

FIG. 7

|  | Control group | Stimulation group |
|---|---|---|
| Heart Rate (beats/min) | 89 ±3 | 89 ±3 |
| Mean AoP (mmHg) | 70 ±4 | 80 ± 3 |
| LV EDP (mmHg) | 11 ±1 | 8 ±1 |
| Peak +dP/dt (mmHg/sec) | 1555 ± 447 | 1489 ± 123 |
| Peak −dP/dt (mmHg/sec) | 1312 ± 80 | 1509 ± 93 |
| Cardiac Output (L/min) | 2.13 ± 0.16 | 2.19 ±0.16 |
| Stroke Volume (ml) | 24 ± 1 | 25 ± 1 |
| LV EDV (ml) | 47 ±3 | 48 ± 3 |
| LV ESV (ml) | 23 ±1 | 23 ± 1 |
| LV Ejection Fraction (%) | 50 ±1 | 52 ± 1 |
| LV EDSI | 1.72 ± 0.09 | 1.53 ± 0.07 |
| LV ESSI | 1.71 ±0.06 | 1.71 ± 0.06 |
| LV FAS (%) | 40 ±1 | 43 ± 2 |
| PE/PA | 2.6 ± 0.4 | 3.2 ± 0.3 |
| Deceleration Time (msec) | 112 ±3 | 123 ± 6 |
| WS (dynes−sec−cm$^{-5}$) | 40 ± 4 | 30 ± 5 |

FIG. 8

|  | Control group | | | Stimulation group | | |
|---|---|---|---|---|---|---|
|  | PRE | POST | Δ | PRE | POST | Δ |
| Heart Rate (beats/min) | 86 ± 2 | 90 ± 1 | 4 ± 3 | 87 ± 3 | 89 ± 3 | 2 ± 3 |
| Mean AoP (mmHg) | 72 ± 5 | 83 ± 5 | 11 ± 3 | 84 ± 3 | 85 ± 3 | 1 ± 3 |
| LV EDP (mmHg) | 14 ± 1 | 15 ± 1 | 1 ± 1 | 15 ± 1 | 11 ± 2 | -4 ± 1 |
| Peak + dP/dt (mmHg/sec) | 1110±81 | 1131±72 | 20±113 | 1315±87 | 1321±60 | 6 ± 87 |
| Peak - dP/dt (mmHg/sec) | 1115±81 | 1253±92 | 139±111 | 1298±86 | 1353±118 | 56 ± 57 |
| Cardiac Output (L/min) | 1.59±0.10 | 1.55±0.05 | -0.04±0.08 | 1.72± 0.17 | 2.10±0.14 | 0.38±0.11 |
| Stroke Volume (ml) | 19 ± 1 | 17 ± 1 | 2 ± 0.4 | 20 ± 2 | 24 ± 1 | 4 ± 1 |
| LV EDV (ml) | 56 ± 2 | 60 ± 2 | 4 ± 1 | 58 ± 4 | 57 ± 4 | -1 ± 2 |
| LV ESV (ml) | 37 ± 1 | 42 ± 2 | 5 ± 1 | 38 ± 2 | 34 ± 3 | -4 ± 1 |
| LV Ejection Fraction (%) | 33 ± 1 | 29 ± 1 | -4 ± 0.2 | 34 ± 1 | 41 ± 2 | 7 ± 1 |
| LV EDSI | 1.53±0.06 | 1.48±0.05 | -0.05±0.02 | 1.44±0.04 | 1.48±0.03 | 0.05±0.02 |
| LV ESSI | 1.59±0.05 | 1.48±0.03 | -0.12±0.04 | 1.55±0.05 | 1.63±0.04 | 0.07±0.04 |
| LV FAS (%) | 25 ± 1 | 20 ± 1 | -5 ± 1 | 26 ± 1 | 32 ± 1 | 6 ± 2 |
| PE/PA | 2.0 ± 0.2 | 1.8 ± 0.2 | -0.2 ± 0.1 | 2.0 ± 0.3 | 2.4 ± 0.4 | 0.4 ± 0.2 |
| Deceleration Time (msec) | 91 ± 1 | 85 ± 4 | -6 ± 3 | 94 ± 5 | 111 ± 10 | 17 ± 7 |
| EDWS (gm/cm2) | 54 ± 4 | 57 ± 4 | 3 ± 4 | 60 ± 5 | 46 ± 8 | -14 ± 3 |
| Severity of MR (%) | 14 ± 3 | 21 ± 2 | 7 ± 3 | 15 ± 3 | 10 ± 2 | -6 ± 2 |

FIG. 9

|  | Normal group | Control group | Stimulation group |
|---|---|---|---|
| VF Replacement Fibrosis (%) | 0 | 21 ± 2 | 13 ± 1 |
| VF Interstitial Fibrosis (%) | 3.7 ± 0.1 | 8.3 ± 0.2 | 6.5 ± 0.3 |
| Capillary Density (cap/mm²) | 2607 ± 80 | 1704 ± 35 | 2403 ± 73 |
| Capillary/Fiber Ratio | 1.0 ± 0 | 0.95 ± 0.02 | 1.20 ± 0.04 |
| Oxygen Diffusion Distance (μm) | 8.9 ± 0.2 | 11.0 ± 0.10 | 9.2 ± 0.1 |
| Myocyte Cross-Sectional Area (μm²) | 409 ± 10 | 720 ± 14 | 549 ± 15 |

NERVE STIMULATION FOR TREATING DISORDERS

CROSS-REFERENCES TO RELATED APPLICATIONS

This application claims the benefit of U.S. Provisional Application Nos. 60/668,275, filed Apr. 4, 2005 and 60/612,428, filed Sep. 23, 2004, the contents of which are hereby incorporated by reference into this application.

FIELD OF THE INVENTION

The present invention relates generally to treating patients by application of electrical signals to a selected nerve or nerve bundle, and specifically to methods and apparatus for stimulating the vagus nerve for treating heart conditions.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including heart failure and atrial fibrillation. Heart failure is a cardiac condition characterized by a deficiency in the ability of the heart to pump blood throughout the body and/or to prevent blood from backing up in the lungs. Customary treatment of heart failure includes medication and lifestyle changes. It is often desirable to lower the heart rates of patients suffering from faster than normal heart rates. The effectiveness of beta blockers in treating heart disease is attributed in part to their heart-rate-lowering effect.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

US Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

PCT Publication WO 04/043494 to Paterson et al., which is incorporated herein by reference, describes methods and products for increasing cardiac vagal responsiveness and vagal tone, and for decreasing sympathetic activity. The methods include delivering, to a patient's cardiac autonomic structures, a nucleic acid, which, when expressed, increases nitric oxide synthase levels.

US Patent Application Publication 2005/0131467 to Boveja, which is incorporated herein by reference, describes techniques for providing pulsed electrical stimulation to vagus nerve(s) for providing therapy for cardiovascular disorders such as atrial fibrillation, congestive heart failure, inappropriate sinus tachycardia, and refractory hypertension.

US Patent Application Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

US Patent Application Publication 2005/0197675, which is assigned to the assignee of the present application and is incorporated herein by reference, describes apparatus including an electrode device, which is adapted to be coupled to a site of a subject, and a control unit, which is adapted to drive the electrode device to apply a current to the site intermittently during alternating "on" and "off" periods, each of the "on" periods having an "on" duration equal to between 1 and 10 seconds, and each of the "off" periods having an "off" duration equal to at least 50% of the "on" duration.

US Patent Application Publication 2004/0193231, which is assigned to the assignee of the present application and is incorporated herein by reference, describes apparatus including an electrode device, which is adapted to be coupled to a vagus nerve of a subject, and a control unit, which is adapted to drive the electrode device to apply to the vagus nerve a current that reduces heart rate variability of the subject.

PCT Publication WO 03/099377 to Ayal et al., which is assigned to the assignee of the present application and is incorporated herein by reference, describes apparatus for treating a subject, including an electrode device, which is adapted to be coupled to a vagus nerve of the subject, and a heart rate sensor, which is configured to detect a heart rate of the subject, and to generate a heart rate signal responsive thereto. The apparatus also includes a control unit, which is adapted to receive the heart rate signal, and, responsive to determining that the heart rate is greater than a threshold value, which threshold value is greater than a normal heart rate, drive the electrode device to apply a current to the vagus nerve, and configure the current so as to reduce the heart rate of the subject.

PCT Publication WO 03/018113 to Cohen et al., which is assigned to the assignee of the present application and is incorporated herein by reference, describes apparatus for treating a condition of a subject, including an electrode device, which is adapted to be coupled to longitudinal nervous tissue of the subject, and a control unit, which is adapted to drive the electrode device to apply to the nervous tissue a current which is capable of inducing action potentials that propagate in the nervous tissue in a first direction, so as to treat the condition. The control unit is further adapted to suppress action potentials from propagating in the nervous tissue in a second direction opposite to the first direction.

U.S. Pat. No. 6,684,105 to Cohen et al., which is assigned to the assignee of the present application and is incorporated herein by reference, describes apparatus for treating a condition of a subject, including an electrode device, which is adapted to be coupled to longitudinal nervous tissue of the subject, and a control unit, which is adapted to drive the electrode device to apply to the nervous tissue a current which is capable of inducing action potentials that propagate in the nervous tissue in a first direction, so as to treat the condition. The control unit is further adapted to suppress action potentials from propagating in the nervous tissue in a second direction opposite to the first direction.

U.S. Pat. No. 6,610,713 to Tracey, which is incorporated herein by reference, describes a method for inhibiting the release of a proinflammatory cytokine in a cell. The method includes treating the cell with a cholinergic agonist. The method is described as being useful in patients at risk for, or suffering from, a condition mediated by an inflammatory cytokine cascade, for example endotoxic shock. The cholinergic agonist treatment is effected by stimulation of an efferent vagus nerve fiber, or the entire vagus nerve.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," *Nervous Control of Vascular Function*, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., *Neural Regulation of the Heart*, Oxford University Press (1977), particularly pages 100-106.

Armour J A et al. eds., *Neurocardiology*, Oxford University Press (1994)

Perez M G et al., "Effect of stimulating non-myelinated vagal axon on atrioventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Fuster V and Ryden L E et al., "ACC/AHA/ESC Practice Guidelines—Executive Summary," J Am Coll Cardiol 38(4): 1231-65 (2001)

Fuster V and Ryden L E et al., "ACC/AHA/ESC Practice Guidelines—Full Text," J Am Coll Cardiol 38(4): 1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4): 198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421: 384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Sabbah H N et al., "A canine model of chronic heart failure produced by multiple sequential coronary microembolizations," Am J Physiol 260:H1379-1384 (1991)

Sabbah H N et al., "Effects of long-term monotherapy with enalapril, metoprolol, and digoxin on the progression of left ventricular dysfunction and dilation in dogs with reduced ejection fraction," Circulation 89:2852-2859 (1994)

Dodge H T et al., "Usefulness and limitations of radiographic methods for determining left ventricular volume," Am J Cardiol 18:10-24 (1966)

Sabbah H N et al., "Left ventricular shape: A factor in the etiology of functional mitral regurgitation in heart failure," Am Heart J 123: 961-966 (1992)

Heart rate variability is considered an important determinant of cardiac function. Heart rate normally fluctuates within a normal range in order to accommodate constantly changing physiological needs. For example, heart rate increases during waking hours, exertion, and inspiration, and decreases during sleeping, relaxation, and expiration. Two representations of heart rate variability are commonly used: (a) the standard deviation of beat-to-beat RR interval differences within a certain time window (i.e., variability in the time domain), and (b) the magnitude of variability as a function of frequency (i.e., variability in the frequency domain).

Short-term (beat-to-beat) variability in heart rate represents fast, high-frequency (HF) changes in heart rate. For example, the changes in heart rate associated with breathing are characterized by a frequency of between about 0.15 and about 0.4 Hz (corresponding to a time constant between about 2.5 and 7 seconds). Low-frequency (LF) changes in heart rate (for example, blood pressure variations) are characterized by a frequency of between about 0.04 and about 0.15 Hz (corresponding to a time constant between about 7 and 25 seconds). Very-low-frequency (VLF) changes in heart rate are characterized by a frequency of between about 0.003 and about 0.04 Hz (0.5 to 5 minutes). Ultra-low-frequency (ULF) changes in heart rate are characterized by a frequency of between about 0.0001 and about 0.003 Hz (5 minutes to 2.75 hours). A commonly used indicator of heart rate variability is the ratio of HF power to LF power.

High heart rate variability (especially in the high frequency range, as described hereinabove) is generally correlated with a good prognosis in conditions such as ischemic heart disease and heart failure. In other conditions, such as atrial fibrillation, increased heart rate variability in an even higher frequency range can cause a reduction in cardiac efficiency by producing beats that arrive too quickly (when the ventricle is not optimally filled) and beats that arrive too late (when the ventricle is fully filled and the pressure is too high).

Kamath et al., in "Effect of vagal nerve electrostimulation on the power spectrum of heart rate variability in man," Pacing Clin Electrophysiol 15:235-43 (1992), describe an increase in the ratio of low frequency to high frequency components of the peak power spectrum of heart rate variability during a period without vagal stimulation, compared to periods with vagal stimulation. Iwao et al., in "Effect of constant and intermittent vagal stimulation on the heart rate and heart rate variability in rabbits," Jpn J Physiol 50:33-9 (2000), describe no change in heart rate variability caused by respiration in all modes of stimulation with respect to baseline data. Each of these articles is incorporated herein by reference.

The following articles, which are incorporated herein by reference, may be of interest:

Kleiger R E et al., "Decreased heart rate variability and its association with increased mortality after myocardial infarction," Am J Cardiol 59: 256-262 (1987)

Akselrod S et al., "Power spectrum analysis of heart rate fluctuation: a quantitative probe of beat-to-beat cardiovascular control," Science 213: 220-222 (1981)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects. The significance of sympathetic and parasympathetic activation are described as being evaluated by determining the effects of autonomic nervous system using vagal and stellar ganglions stimulation, and by using autonomic nervous system neurotransmitters infusion (norepinephrine, acetylcholine).

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. No. 5,334,221 to Bardy and U.S. Pat. No. 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electro-stimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

A number of patents and articles describe other methods and devices for stimulating nerves to achieve a desired effect. Often these techniques include a design for an electrode or electrode cuff.

US Patent Application Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

Levy M N, Blattberg B., "Effect of vagal stimulation on the overflow of norepinephrine into the coronary sinus during sympathetic nerve stimulation in the dog," Circ Res 1976 February; 38(2):81-4

Lavallee et al. "Muscarinic inhibition of endogenous myocardial catecholamine liberation in the dog," Can J Physiol Pharmacol 1978 August; 56(4):642-9

Mann D L, Kent R L, Parsons B, Cooper G, "Adrenergic effects on the biology of the adult mammalian cardiocyte," Circulation 1992 February; 85(2):790-804

Mann D L, "Basic mechanisms of disease progression in the failing heart: role of excessive adrenergic drive," Prog Cardiovasc Dis 1998 July-August; 41(1suppl 1):1-8

Barzilai A, Daily D, Zilkha-Falb R, Ziv I, Offen D, Melamed E, Sirv A, "The molecular mechanisms of dopamine toxicity," Adv Neurol 2003; 91:73-82

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection.

Nitric oxide is an important signaling molecule that acts in many tissues to regulate a diverse range of physiological processes, including: (a) vasodilation or vasoconstriction, with resulting changes in blood pressure and blood flow, (b) neurotransmission in the central and peripheral nervous system, including mediation of signals for normal gastrointestinal motility, and (c) defense against pathogens such as bacteria, fungus, and parasites due to the toxicity of high levels of NO to pathogenic organisms.

NO is synthesized within cells by three NO synthases (NOSs):

Neuronal NOS (nNOS), also known as NOS-1, which is regulated by calcium/calcium-calmodulin;

Inducible NOS (iNOS), also known as NOS-2, which is cytokine-inducible and calcium-independent; and Endothelial NOS (eNOS), also known as NOS-3, which is regulated by calcium/calcium-calmodulin enzymes.

The major roles of nitric oxide include:

vasodilation or vasoconstriction, with resulting changes in blood pressure and blood flow;

neurotransmission in the central and peripheral nervous system, including mediation of signals for normal gastrointestinal motility; and defense against pathogens such as bacteria, fungus, and parasites, because of the toxicity of high levels of NO to pathogenic organisms.

In blood vessels, NOS-3 mediates endothelium-dependent vasodilation in response to acetylcholine, bradykinin, and other mediators. NO also maintains basal vascular tone and regulates regional blood flow. NO levels increase in response to shear stress (Furchgott et al., and Ignarro (1989) (this and the following references are cited hereinbelow)).

In the nervous system, NOS-1 is localized to discrete populations of neurons in the cerebellum, olfactory bulb, hippocampus, cortex, striatum, basal forebrain, and brain stem. NO plays a role in nervous system morphogenesis and synaptic plasticity. NO is used as a neurotransmitter particularly for long-term potentiation, which is essential for learning and memory (Bishop et al.). The central nervous system immune cell counterparts, microglia and astrocytes, also synthesize NOS-2, which generates a burst of NO in response to injury. Upregulation of NOS expression is seen in many neurodegenerative diseases and in injury. In the peripheral nervous system, NO mediates relaxation of smooth muscle. NOS-containing neurons also innervate the corpora cavernosa of the penis. Stimulation of these nerves can lead to penile erection and dilation of cerebral arteries, respectively (Snyder, Schmidt et al.).

In the immune system, NO is produced by cytokine-activated macrophages and neutrophils as a cytotoxic agent. High concentrations of NO produced in these cells kill target cells, such as tumor cells and pathogens. In inflammation, a number of factors upregulate NOS-2, including interleukins, interferon-gamma, TNF-alpha, and LPS (Nathan, Marletta (1993), Salvemini (1998)). NOS-2 also plays an important role in innate immunity (Bogdan et al.). A role for constitutive NOS (i.e., NOS expressed without stimulation) and NOS-2 has been demonstrated in an experimental model of bacterial component-induced joint inflammation and tissue degradation (Whal et al. (2003)).

NOSs exert a large number of biological effects in the cardiovascular system. NOSs modulate myocardial oxygen consumption, enhance perfusion-contraction matching and mechanical efficiency, influence cardiac substrate utilization, and prevent apoptosis (Massion et al.). A decrease in the expression of NOS-3 occurs in heart failure. NOS-3 produces low concentrations of NO which is believed necessary for good endothelial function and integrity, and is viewed as a protective agent in a variety of diseases including heart failure, because it plays an important role in the control of myocardial oxygen consumption. Mice deficient in NOS-3 develop postnatal heart failure. Lack of NOS-3 decreases vascular endothelial growth factor (VEGF) expression, and can impair angiogenesis and capillary development that can contribute to cardiac abnormalities. Increased expression of cytokines (in particular, tumor necrosis factor (TNF), such as in heart failure) can induce downregulation of NOS-3. Reduced NOS-3 in heart failure increases the activity of caspase 3, and thus can trigger cardiomyocytes' apoptosis or programmed cell death. (Ferreiro et al.)

Feron et al. showed that agonist binding to muscarinic acetylcholine (mAchRs) receptors on cardiomyocytes results in the activation of NOS-3. Balligand et al. showed that NOS inhibitors reduce the influence of muscarinic agonists on the spontaneous beating rate of rat cardiac myocytes. They also showed that NOS inhibitors increased the inotropic effect of the beta-adrenergic agonist isoproterenol on electrically stimulated adult rat ventricular myocytes. They thus concluded that NOS can protect the heart against excessive stimulation by catecholamines, just as an endogenous beta-blocker. Massion et al. confirmed that NOS-3 attenuates beta adrenergic activity by showing that overexpression of NOS-3 in mice increases the negative chronotropic effect of carbamylcholine as well as attenuated the b-adrenergic positive inotropic effect of isoproterenol. Bendall et al. demonstrated that cardiac NOS-1 expression significantly increased in failing hearts. Failing hearts exposed to NOS-1 inhibition demonstrated better left ventricular function.

Ziolo et al. showed that high levels of iNOS contribute to blunted beta-adrenergic response in failing human hearts by decreasing Ca2+ transients. The presence of systemic inflammation determined by elevations in C-reactive protein (CRP) has been associated with persistence of atrial fibrillation (AF). CRP measurement and cardiovascular assessment were performed at baseline in 5806 subjects. Elevated CRP predicted increased risk for developing future AF (Aviles et al.).

NOS enzymes play critical roles in the physiology and pathophysiology of neuronal, renal, pulmonary, gastrointestinal, skeletal muscle, reproductive, and cardiovascular biology.

All NOS isoforms are involved in promoting or inhibiting the etiology of cancer. NOS activity has been detected in tumor cells of various origins and has been associated with tumor grade, proliferation rate, and expression (Xu et al., Ignarro (1989), Jaiswal (2001)). NOS stimulates angiogenesis, and correlates with tumor growth and aggressiveness (Morbidelli).

Upregulation of NOS expression occurs in many neurodegenerative diseases, including Alzheimer's disease, dementia, stress, and depression (Togo et al., and McLeod et al.). NO mediates relaxation of smooth muscle in the gut, and peristalsis.

NO is an important neurohumoral modulator of renal hemodynamics. NO serves as a neurotransmitter in the lower urinary tract, affects relaxation of the bladder and urethra, and also affects overactive bladder, bladder outlet obstruction, diabetic cystopathy, interstitial cystitis, and bladder inflammation (Ho).

NOS has been reported to be expressed and to play a role in white adipose tissue (Fruhbeck).

NOS plays multiple roles in airway physiology and pathophysiology. In the respiratory tract, NO adduct molecules (nitrosothiols) have been shown to be modulators of bronchomotor tone. The concentration of this molecule in exhaled air is abnormal in activated states of different inflammatory airway diseases, and asthma (Ricciardolo et al.).

In diabetic mellitus, alterations in production of the NOS-3/NO system cause angiopathy and death. Hyperglycemia causes NOS uncoupling, which results in a perturbation of the physiological properties of NO. Abnormality in NO availability thus results in generalized accelerated atherosclerosis, hyperfiltration, glomerulosclerosis, tubulointerstitial fibrosis and progressive decline in glomerular filtration rate, and apoptosis and neovascularization in the retina (Santilli et al.).

Increased expression of NOS-1 has been found in both chronic and acute hepatic encephalopathy (Rao).

The following articles, which are incorporated herein by reference, may be of interest:

Furchgott R F et al., "Endothelium-derived relaxing and contracting factors," FASEB J 3:2007-2018 (1989)

Ignarro L J, "Endothelium-derived nitric oxide: actions and properties," FASEB J 3:31-36. (1989)

Ignarro L J, Introduction and overview, in Ignarro L J, Editors, *Nitric Oxide: Biology and Pathobiology*, Academic Press, San Diego, Calif. (2000), pp. 3-19.

Schmidt H H H W et al., "NO at Work," Cell 78:919-925 (1994)

Snyder S H, "No endothelial NO," Nature 377:196-197 (1995)

Jaiswal N F et al., "Nitric oxide in gastrointestinal epithelial cell carcinogenesis: linking inflammation to carcinogenesis," Am J Physiol Gastroint Liver Physiol 281:G626-G634 (2001)

Chinthalapally V et al., "Nitric oxide signaling in colon cancer chemoprevention," Mutat Res 555(1-2):107-19 (2004)

Ho M H et al., "Physiologic role of nitric oxide and nitric oxide synthase in female lower urinary tract," Curr Opin Obstet Gynecol 16(5):423-9 (2004)

Fruhbeck G, "The adipose tissue as a source of vasoactive factors," Curr Med Chem Cardiovasc Hematol Agents 2(3): 197-208 (2004)

Marletta M A, "Nitric Oxide Synthase Structure and Mechanism," J Biol Chem 268:12231-12234 (1993)

Nathan C, "Nitric oxide as a secretory product of mammalian cells," FASEB J 6:3051-3064 (1992)

Ricciardolo F L, et al., "Nitric oxide in health and disease of the respiratory system," Physiol Rev 84(3):731-65 (2004)

Bishop A et al., "NO signaling in the CNS: from the physiological to the pathological," Toxicology 208:193-205 (2005)

Togo T et al., "Nitric oxide pathways in Alzheimer's disease and other neurodegenerative dementias," Neurol Res 26(5):563-6 (2004)

Santilli F et al., "The role of nitric oxide in the development of diabetic angiopathy," Horm Metab Res 36(5):319-35 (2004)

Xu W et al., "The role of nitric oxide in cancer," Cell Res 12(5-6):311-20 (2002)

Morbidelli L et al., "Role of nitric oxide in the modulation of angiogenesis," Curr Pharm Des 9(7):521-30 (2003)

McLeod T et al., "Nitric oxide, stress, and depression," Psychopharmacol Bull 35(1):24-41 (2001)

Whitworth J A et al., "The nitric oxide system in glucocorticoid-induced hypertension," J Hypertens 20(6):1035-43 (2002)

Rao V L, "Nitric oxide in hepatic encephalopathy and hyperammonemia," Neurochem Int 41(2-3):161-70 (2002)

Blantz R C et al., "The complex role of nitric oxide in the regulation of glomerular ultrafiltration," Kidney Int 61(3): 782-5 (2002)

Wahl S M et al., "Nitric oxide in experimental joint inflammation. Benefit or detriment?" Cells Tissues Organs 174 (1-2):26-33 (2003)

Massion P B et al., "Regulation of the mammalian heart function by nitric oxide," Comp Biochem Physiol A Mol Integr Physiol 2005 Jun. 25 [epublication ahead of print]

Bogdan C et al., "The role of nitric oxide in innate immunity," Immunol Rev 173:17-26 (2000)

Salvemini D et al., "Inducible nitric oxide synthase and inflammation," Expert Opin Investig Drugs 7(1):65-75 (1998)

Balligand J L et al., "Abnormal contractile function due to induction of nitric oxide synthesis in rat cardiac myocytes follows exposure to activated macrophage-conditioned medium," J Clin Invest 91:2314-2319 (1993)

Feron O et al., "Dynamic targeting of the agonist-stimulated m2 muscarinic acetylcholine receptor to caveolae in cardiac myocytes," J Biol Chem 272:17744-17748 (1997)

Bendall J K et al., "Role of myocardial neuronal nitric oxide synthase-derived nitric oxide in beta-adrenergic hyporesponsiveness after myocardial infarction-induced heart failure in rat," Circulation 110(16):2368-75 (2004) Epub 2004 Oct. 4

Ziolo M T et al., "Myocyte nitric oxide synthase 2 contributes to blunted beta-adrenergic response in failing human hearts by decreasing Ca2+ transients," Circulation 109(15):1886-91 (2004) Epub 2004 Mar. 22

Aviles R J et al., "Inflammation as a Risk Factor for Atrial Fibrillation," Circulation 108:3006-3010 (2003)

Bruins P et al., "Activation of the complement system during and after cardiopulmonary bypass surgery: postsurgery activation involves C-reactive protein and is associated with postoperative arrhythmia," Circulation 96(10):3542-3548 (1997)

Frustaci A et al., "Histological substrate of atrial biopsies in patients with lone atrial fibrillation," Circulation 96(4): 1180-1184 (1997)

Mihm M J et al., "Impaired myofibrillar energetics and oxidative injury during human atrial fibrillation," Circulation 104(2):174-180 (2001)

Marin F et al., "Factor XIII Val34Leu polymorphism modulates the prothrombotic and inflammatory state associated with atrial fibrillation," J Mol Cell Cardiol 37:699-704 (2004)

Gaudino M et al., "The −174G/C interleukin-6 polymorphism influences postoperative interleukin-6 levels and postoperative atrial fibrillation. Is atrial fibrillation an inflammatory complication?" Circulation 108 (Suppl. 1): II195-199 (2003)

Chung M K et al., "C-reactive protein elevation in patients with atrial arrhythmias: inflammatory mechanisms and persistence of atrial fibrillation," Circulation 104(24): 2886-2891 (2001)

Conway D S et al., "Predictive value of indexes of inflammation and hypercoagulability on success of cardioversion of persistent atrial fibrillation," Am J Cardiol 94:508-510 (2004)

Dernellis J et al., "C-reactive protein and paroxysmal atrial fibrillation: evidence of the implication of an inflammatory process in paroxysmal atrial fibrillation," Acta Cardiol 56:375-380 (2001)

Korantzopoulos P et al., "Variation of inflammatory indexes after electrical cardioversion of persistent atrial fibrillation. Is there an association with early recurrence rates?" Int J Clin Pract 59(8):881-885 (2005)

Ferreiro C R et al., "Expression of inducible nitric oxide synthase is increased in patients with heart failure due to ischemic disease," Braz J Med Biol Res. 37(9):1313-20 (2004) Epub 2004 Aug. 24

Mak B C et al., "Aberrant beta-catenin signaling in tuberous sclerosis," Am J Pathol 167(1):107-16 (2005)

Gould V E et al., "The phosphorylated form of connexin43 is up-regulated in breast hyperplasias and carcinomas and in their neoformed capillaries," Hum Pathol 36(5):536-45 (2005)

Haass N K et al., "The role of altered cell-cell communication in melanoma progression," J Mol Histol 35(3):309-18 (2004)

Marino A A et al., Increased intercellular communication through gap junctions may contribute to progression of osteoarthritis," Clin Orthop Relat Res (422):224-32 (2004)

Brandner J M et al., "Connexins 26, 30, and 43: differences among spontaneous, chronic, and accelerated human wound healing," J Invest Dermatol 122(5):1310-20 (2004)

Gajda Z et al., "Involvement of gap junctions in the manifestation and control of the duration of seizures in rats in vivo," Epilepsia 44(12):1596-600 (2003)

Christ G J et al., "Increased connexin43-mediated intercellular communication in a rat model of bladder overactivity in vivo," Am J Physiol Regul Integr Comp Physiol 284(5): R1241-8 (2003)

Haefliger J A et al., "Connexins 43 and 26 are differentially increased after rat bladder outlet obstruction," Exp Cell Res 274(2):216-25 (2002)

Vis J C et al., "Connexin expression in Huntington's diseased human brain," Cell Biol Int 22(11-12):837-47 (1998)

Nagy J I et al., "Elevated connexin43 immunoreactivity at sites of amyloid plaques in Alzheimer's disease," Brain Res 717(1-2): 173-8 (1996)

Wahl S M et al., "Nitric oxide in experimental joint inflammation. Benefit or detriment?" Cells Tissues Organs 174 (1-2):26-33 (2003)

Ilebekk et al., "Influence of endogenous neuropeptide Y (NPY) on the sympathetic-parasympathetic interaction in the canine heart," Cardiovasc Pharmacol 46(4):474-480 (2005)

Danson et al., "Cardiac nitric oxide: Emerging role for nNOS in regulating physiological function," Pharmacol Ther 106 (1):57-74 (2005)

SUMMARY OF THE INVENTION

In some embodiments of the present invention, apparatus for treating a heart condition comprises a multipolar electrode device that is applied to a portion of a vagus nerve that innervates the heart of a patient. Typically, the system is configured to treat heart failure and/or heart arrhythmia, such as atrial fibrillation or tachycardia. A control unit typically drives the electrode device to (i) apply signals to induce the propagation of efferent action potentials towards the heart, and (ii) suppress artificially-induced afferent and efferent action potentials, in order to minimize any unintended side effect of the signal application. Alternatively, the control unit drives the electrode device to apply signals that induce symmetric or asymmetric bi-directional propagation of nerve impulses.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, a small anodal current is applied in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked, as described above. By not stimulating large-diameter fibers, such stimulation generally avoids adverse effects sometimes associated with recruitment of such large fibers, such as dyspnea and hoarseness. Stimulation of small-diameter fibers is avoided because these fibers transmit pain sensations and are important for regulation of reflexes such as respiratory reflexes. Alternatively, the control unit is configured to apply a current that does not select for fibers of particular diameters.

In some embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set typically comprises a plurality of anodes in order to minimize the virtual cathode effect in the direction of the brain.

In some embodiments of the present invention, the efferent and afferent anode sets each comprise exactly one electrode, which are directly electrically coupled to each other. The cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, an anodal current is applied in order to inhibit action potentials induced by the cathodic current in the large-diameter fibers (e.g., A-fibers), but not in the small- and medium-diameter fibers (e.g., B- and C-fibers). This combination of cathodic and anodal current generally results in the stimulation of medium-diameter fibers (e.g., B-fibers) only.

Typically, parasympathetic stimulation of the vagus nerve is applied responsive to one or more sensed physiological parameters or other parameters, such as heart rate, electrocardiogram (ECG), blood pressure, indicators of cardiac contractility, cardiac output, norepinephrine concentration, baroreflex sensitivity, or motion of the patient. Typically, stimulation is applied in a closed-loop system in order to achieve and maintain a desired heart rate responsive to one or more such sensed parameters. For some applications, such stimulation is applied chronically, i.e., during a period having a duration of at least one week, e.g., at least one month.

In some embodiments of the present invention, vagal stimulation is applied in a burst (i.e., a series of pulses). The application of the burst in each cardiac cycle typically commences after a variable delay after a detected R-wave, P-wave, or other feature of an ECG. The delay is typically calculated in real time using a function, the inputs of which include one or more pre-programmed but updateable constants and one or more sensed parameters, such as the R-R interval between cardiac cycles and/or the P-R interval. Alternatively or additionally, a lookup table of delays is used to determine in real time the appropriate delay for each application of pulses, based on the one or more sensed parameters.

In some embodiments of the present invention, the control unit is configured to drive the electrode device to stimulate the vagus nerve so as to reduce the heart rate of the subject towards a target heart rate. Parameters of stimulation are varied in real time in order to vary the heart-rate-lowering effects of the stimulation. In embodiments of the present invention in which the stimulation is applied in a series of pulses that are synchronized with the cardiac cycle of the subject, such as described hereinabove, parameters of such pulse series typically include, but are not limited to: (a) timing of the stimulation within the cardiac cycle, (b) pulse duration (width), (c) pulse repetition interval, (d) pulse period, (e) number of pulses per burst, also referred to herein as "pulses per trigger" (PPT), (f) amplitude, (g) duty cycle, (h) choice of vagus nerve, and (i) "on"/"off" ratio and timing (i.e., during intermittent operation).

In some embodiments of the present invention, the control unit is configured to drive the electrode device to stimulate the vagus nerve so as to modify heart rate variability of the subject. For some applications, the control unit is configured to apply stimulation with parameters that tend to or that are selected to reduce heart rate variability, while for other applications parameters are used that tend to or that are selected to increase variability. For some applications, the parameters of the stimulation are selected to both reduce the heart rate of the subject and heart rate variability of the subject. For other applications, the parameters are selected to reduce heart rate variability while substantially not reducing the heart rate of the subject. For some applications, the control unit is configured to drive the electrode device to stimulate the vagus nerve so as to modify heart rate variability in order to treat a condition of the subject.

Advantageously, the techniques described herein generally enable relatively fine control of the level of stimulation of the vagus nerve, by imitating the natural physiological smaller-to-larger diameter recruitment order of nerve fibers. This recruitment order allows improved and more natural control over the heart rate. Such fine control is particularly advantageous when applied in a closed-loop system, wherein such control results in smaller changes in heart rate and lower latencies in the control loop, which generally contribute to greater loop stability and reduced loop stabilization time.

"Heart failure," as used in the specification and the claims, is to be understood to include all forms of heart failure, including ischemic heart failure, non-ischemic heart failure, and diastolic heart failure.

"Vagus nerve," and derivatives thereof, as used in the specification and the claims, is to be understood to include portions of the left vagus nerve, the right vagus nerve, the cervical vagus nerve, branches of the vagus nerve such as the superior cardiac nerve, superior cardiac branch, and inferior cardiac branch, and the vagus trunk. Similarly, stimulation of the vagus nerve is described herein by way of illustration and not limitation, and it is to be understood that in some embodiments of the present invention, other autonomic and/or parasympathetic nerves and/or parasympathetic tissue are stimulated, including sites where the vagus nerve innervates a target organ, vagal ganglions, nerves in the epicardial fat pads, a carotid artery, a jugular vein (e.g., an internal jugular vein), a carotid sinus, a coronary sinus, a vena cava vein, a pulmonary vein, and/or a right ventricle, for treatment of heart conditions or other conditions.

There is therefore provided, in accordance with an embodiment of the present invention, apparatus for treating a condition of a subject, including:

an electrode device, adapted to be coupled to an autonomic nerve of the subject; and a control unit, adapted to:

drive the electrode device to apply to the nerve a stimulating current, which is capable of inducing action potentials in a therapeutic direction in a first set and a second set of nerve fibers of the nerve, and drive the electrode device to apply to the nerve an inhibiting current, which is capable of inhibiting the induced action potentials traveling in the therapeutic direction in the second set of nerve fibers, the nerve fibers in the second set having generally larger diameters than the nerve fibers in the first set.

It is to be understood that for some applications the stimulating current may also be capable of inducing action potentials in a non-therapeutic direction opposite the therapeutic direction, and that this embodiment of the present invention is not limited to application of a stimulating current that is capable of inducing action potentials only in a therapeutic direction.

In an embodiment of the present invention, the electrode device is adapted to be coupled to parasympathetic nervous tissue of the subject, and the control unit is adapted to drive the electrode device to apply to the tissue a stimulating current that is not necessarily configured to stimulate only a subset of nerve fibers of the tissue.

In an embodiment, the autonomic nerve includes a parasympathetic nerve of the subject, and the electrode device is adapted to be coupled to the parasympathetic nerve.

In an embodiment, the control unit is adapted to configure the stimulating current to treat one or more of the following conditions of the subject: heart failure, atrial fibrillation, angina, cardiac arrest, arrhythmia, myocardial infarction, hypertension, endocarditis, myocarditis, asthma, an allergy, a neoplastic disorder, rheumatoid arthritis, septic shock, hepatitis, hypertension, diabetes mellitus, an autoimmune disease, a gastric ulcer, a neurological disorder, pain, a migraine headache, peripheral neuropathy, an addiction, a psychiatric disorder, obesity, an eating disorder, impotence, a skin disease, an infectious disease, a vascular disease, a kidney disorder, and a urinary tract disorder.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat heart failure of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat atrial fibrillation of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat angina of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat cardiac arrest of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat arrhythmia of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat myocardial infarction of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat hypertension of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat endocarditis of the subject.

In an embodiment, the nerve includes a vagus nerve of the subject, the electrode device is adapted to be coupled to the vagus nerve, and the control unit is adapted to configure the stimulating current to change a physiological parameter of the subject selected from the list consisting of: a hemodynamic parameter, and a cardiac geometry parameter, sufficiently to treat myocarditis of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat heart failure of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat atrial fibrillation of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat angina of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat cardiac arrest of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat arrhythmia of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat myocardial infarction of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat hypertension of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat endocarditis of the subject.

In an embodiment, the nerve includes a vagus nerve of the subject, the electrode device is adapted to be coupled to the vagus nerve, and the control unit is adapted to configure the stimulating current to change a myocardial cellular anatomy parameter of the subject sufficiently to treat myocarditis of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a stimulation-treatable condition of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a portion of a body of the subject selected from the list consisting of: a heart, a brain, lungs, an organ of a respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to attenuate muscle contractility of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat heart failure of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat atrial fibrillation of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat angina of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat cardiac arrest of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat arrhythmia of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat myocardial infarction of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat hypertension of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat endocarditis of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat myocarditis of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat asthma of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat an allergy of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a neoplastic disorder of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat rheumatoid arthritis of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat septic shock of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat hepatitis of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat hypertension of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat diabetes mellitus of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat an autoimmune disease of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a gastric ulcer of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a neurological disorder of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat pain of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a migraine headache of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat peripheral neuropathy of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat an addiction of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a psychiatric disorder of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat obesity of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat an eating disorder of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat impotence of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a skin disease of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat an infectious disease of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a vascular disease of the subject.

In an embodiment, the nerve includes a vagus nerve of the subject, the electrode device is adapted to be coupled to the vagus nerve, and the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein, sufficiently to treat a disorder of the subject selected from the list consisting of: a kidney disorder, and a urinary tract disorder.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat heart failure of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat atrial fibrillation of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat angina of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat cardiac arrest of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat arrhythmia of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat myocardial infarction of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat hypertension of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat endocarditis of the subject.

In an embodiment, the nerve includes a vagus nerve of the subject, the electrode device is adapted to be coupled to the vagus nerve, and the control unit is adapted to configure the stimulating current to change a level of a neurohormone peptide selected from the list consisting of: N-terminal pro-brain natriuretic peptide (NT-pro-BNP), and a catecholamine, sufficiently to treat myocarditis of the subject.

In an embodiment, the nerve includes a vagus nerve of the subject, the electrode device is adapted to be coupled to the vagus nerve, the subject has undergone a coronary artery bypass graft (CABG) procedure, and the control unit is adapted to configure the stimulating current to suppress at least one of: post-CABG inflammation and post-CABG atrial fibrillation.

In an embodiment, the apparatus includes an electrical cardioversion device, the subject is suffering from atrial fibrillation, and the control unit is adapted to configure the stimulating current to suppress inflammation of the subject, and, thereafter, drive the cardioversion device to apply cardioversion treatment to the subject.

In an embodiment, the inhibiting current includes a first inhibiting current, and the control unit is adapted to drive the electrode device to apply to the nerve a second inhibiting current, which is capable of inhibiting device-induced action potentials traveling in a non-therapeutic direction opposite the therapeutic direction in the first and second sets of nerve fibers.

In an embodiment, the electrode device includes a cathode, adapted to apply the stimulating current, and a primary set of anodes, adapted to apply the inhibiting current. For some applications, the primary set of anodes includes a primary anode and a secondary anode, adapted to be disposed so that the primary anode is located between the secondary anode and the cathode, and the secondary anode is adapted to apply a current with an amplitude less than about one half an amplitude of a current applied by the primary anode.

In an embodiment, the nerve includes a vagus nerve of the subject, the electrode device is adapted to be coupled to the vagus nerve, and the control unit is adapted to configure the stimulating current to change a level of at least one NO synthase of the subject selected from the list consisting of: NOS-1, NOS-2, and NOS-3. For some applications, the control unit is adapted to configure the stimulating current to reduce the level of NOS-1 and the level of NOS-2, and to increase the level of NOS-3. For some applications, the control unit is adapted to apply the stimulating and inhibiting currents during a period having a duration of at least one week.

For some applications, the control unit is adapted to configure the stimulating current to change the level of the at least one NO synthase by an amount sufficient to treat a stimulation-treatable condition of the subject.

For some applications, the control unit is adapted to configure the stimulating current to change the level of the at least one NO synthase by an amount sufficient to treat a portion of a body of the subject selected from the list consisting of: a brain, lungs, an organ of a respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex.

For some applications, the control unit is adapted to configure the stimulating current to change the level of the at least one NO synthase by an amount sufficient to attenuate muscle contractility of the subject.

For some applications, the control unit is adapted to configure the stimulating current to change the level of the at least one NO synthase of heart tissue of the subject. For some applications, the control unit is adapted to configure the stimulating current to change the level of the at least one NO synthase of the heart tissue by an amount sufficient to treat heart failure of the subject. For some applications, the control unit is adapted to apply the stimulating and inhibiting currents during a period having a duration of at least one week.

For some applications, the control unit is adapted to configure the stimulating current to change the level of the at least one NO synthase of the heart tissue by an amount sufficient to treat atrial fibrillation of the subject. For some applications, the control unit is adapted to apply the stimulating and inhibiting currents during a period having a duration of at least one week.

For some applications, the control unit is adapted to configure the stimulating current to change the level of the at least one NO synthase of the heart tissue by an amount sufficient to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

For some applications, the control unit is adapted to configure the stimulating current to change the level of the at least one NO synthase of the heart tissue by an amount sufficient to treat one or more of the following conditions of the subject: angina, cardiac arrest, arrhythmia, myocardial infarction, hypertension, endocarditis, myocarditis, asthma, an allergy, a neoplastic disorder, rheumatoid arthritis, septic shock, hepatitis, hypertension, diabetes mellitus, an autoimmune disease, a gastric ulcer, a neurological disorder, pain, a migraine headache, peripheral neuropathy, an addiction, a psychiatric disorder, obesity, an eating disorder, impotence, a skin disease, an infectious disease, a vascular disease, a kidney disorder, and a urinary tract disorder.

In an embodiment, the nerve includes a vagus nerve of the subject, the electrode device is adapted to be coupled to the vagus nerve, and the control unit is adapted to configure the stimulating current to suppress inflammation of the subject.

For some applications, the control unit is adapted to configure the stimulating current to suppress the inflammation sufficiently to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

For some applications, the control unit is adapted to configure the stimulating current to suppress the inflammation sufficiently to treat a stimulation-treatable condition of the subject.

For some applications, the control unit is adapted to configure the stimulating current to suppress inflammation sufficiently to treat heart failure of the subject.

For some applications, the control unit is adapted to configure the stimulating current to suppress inflammation sufficiently to treat atrial fibrillation of the subject. For some applications, the control unit is adapted to configure the stimulating current to reduce thromboembolism of the subject. For some applications, the control unit is adapted to configure the stimulating current to increase a likelihood of successful cardioversion.

In an embodiment, the nerve includes a vagus nerve of the subject, the electrode device is adapted to be coupled to the vagus nerve, and the control unit is adapted to configure the stimulating current to inhibit release of a proinflammatory cytokine.

For some applications, the control unit is adapted to configure the stimulating current to inhibit the release of the proinflammatory cytokine sufficiently to treat heart failure of the subject. For some applications, the control unit is adapted to configure the stimulating current to inhibit the release of the proinflammatory cytokine sufficiently to treat atrial fibrillation of the subject.

For some applications, the control unit is adapted to apply the stimulating and inhibiting currents during a period having a duration of at least one week. For some applications, the control unit is adapted to configure the stimulating current to inhibit the release of the proinflammatory cytokine sufficiently to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock. For some applications, the control unit is adapted to configure the stimulating current to inhibit the release of the proinflammatory cytokine sufficiently to treat a stimulation-treatable condition of the subject.

In an embodiment, the nerve includes a vagus nerve of the subject, the electrode device is adapted to be coupled to the vagus nerve, and the control unit is adapted to configure the stimulating current to inhibit release of C-reactive protein.

For some applications, the control unit is adapted to configure the stimulating current to inhibit the release of the C-reactive protein sufficiently to treat heart failure of the subject. For some applications, the control unit is adapted to configure the stimulating current to inhibit the release of the C-reactive protein sufficiently to treat atrial fibrillation of the subject. For some applications, the control unit is adapted to apply the stimulating and inhibiting currents during a period having a duration of at least one week.

In an embodiment, the nerve includes a vagus nerve of the subject, the electrode device is adapted to be coupled to the vagus nerve, and the control unit is adapted to configure the stimulating current to change a level of N-terminal pro-brain natriuretic peptide (NT-pro-BNP). For some applications, the control unit is adapted to configure the stimulating current to change the level of NT-pro-BNP by an amount sufficient to treat heart failure of the subject. For some applications, the control unit is adapted to configure the stimulating current to change the level of NT-pro-BNP by an amount sufficient to treat atrial fibrillation of the subject. For some applications, the control unit is adapted to apply the stimulating and inhibiting currents during a period having a duration of at least one week.

In an embodiment, the nerve includes a vagus nerve of the subject, the electrode device is adapted to be coupled to the vagus nerve, and the control unit is adapted to configure the stimulating current to change a level of Connexin 43. For some applications, the control unit is adapted to configure the stimulating current to change the level of Connexin 43 by an amount sufficient to treat one or more of the following conditions of the subject: heart failure, atrial fibrillation, angina, cardiac arrest, arrhythmia, myocardial infarction, hypertension, endocarditis, and myocarditis.

For some applications, the control unit is adapted to apply the stimulating and inhibiting currents during a period having a duration of at least one week.

For some applications, the control unit is adapted to configure the stimulating current to change the level of Connexin 43 by an amount sufficient to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

For some applications, the control unit is adapted to configure the stimulating current to change the level of Connexin 43 by an amount sufficient to treat a portion of a body of the subject selected from the list consisting of: a heart, a brain, lungs, an organ of a respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex.

For some applications, the control unit is adapted to configure the stimulating current to change the level of Connexin 43 by an amount sufficient to treat a condition of the subject selected from the list consisting of: tuberous sclerosis, breast cancer, carcinomas, melanoma, osteoarthritis, a wound, a seizure, bladder overactivity, bladder outlet obstruction, Huntington's disease, and Alzheimer's disease.

For some applications, the autonomic nerve includes a lacrimal nerve, and the control unit is adapted to drive the electrode device to apply the stimulating and inhibiting currents to the lacrimal nerve. For some applications, the autonomic nerve includes a salivary nerve, and the control unit is adapted to drive the electrode device to apply the stimulating and inhibiting currents to the salivary nerve. For some applications, the autonomic nerve includes a pelvic splanchnic nerve, and the control unit is adapted to drive the electrode device to apply the stimulating and inhibiting currents to the pelvic splanchnic nerve.

In an embodiment, the autonomic nerve includes a sympathetic nerve, and the control unit is adapted to drive the electrode device to apply the stimulating and inhibiting currents to the sympathetic nerve.

For some applications, the control unit is adapted to drive the electrode device to apply the stimulating and inhibiting currents to the nerve so as to affect behavior of one or more of the following organs of the subject, so as to treat the condition: a stomach, a pancreas, a small intestine, a liver, a spleen, a kidney, a bladder, a rectum, a large intestine, a reproductive organ, and an adrenal gland.

There is also provided, in accordance with an embodiment of the present invention, a method for treating a condition of a subject, including:

applying, to an autonomic nerve of the subject, a stimulating current which is capable of inducing action potentials in a therapeutic direction in a first set and a second set of nerve fibers of the nerve; and applying to the nerve an inhibiting current which is capable of inhibiting the induced action potentials traveling in the therapeutic direction in the second set of nerve fibers, the nerve fibers in the second set having generally larger diameters than the nerve fibers in the first set.

In an embodiment, the autonomic nerve includes a parasympathetic nerve of the subject, and applying the stimulating current includes applying the stimulating current to the parasympathetic nerve.

In an embodiment, the method includes identifying a clinical benefit for the subject to experience a change in a level of at least one NO synthase of the subject selected from the list consisting of: NOS-1, NOS-2, and NOS-3; the nerve includes a vagus nerve of the subject; applying the stimulating and inhibiting currents includes applying the stimulating and inhibiting currents to the vagus nerve; and applying the stimulating current includes configuring the stimulating current to change the level of the at least one NO synthase.

There is further provided, in accordance with an embodiment of the present invention, apparatus for treating a condition of a subject, including:

an electrode device, adapted to be coupled to parasympathetic nervous tissue of the subject; and a control unit, adapted to drive the electrode device to apply a stimulating current to the tissue, and to configure the stimulating current to change a level of at least one NO synthase of the subject selected from the list consisting of: NOS-1, NOS-2, and NOS-3.

For some applications, the control unit is adapted to configure the stimulating current to reduce the level of NOS-1 and the level of NOS-2, and to increase the level of NOS-3.

For some applications, the control unit is adapted to apply the stimulating current during a period having a duration of at least one week.

In an embodiment, the control unit is adapted to configure the stimulating current to change the level of the at least one NO synthase of heart tissue of the subject.

For some applications, the control unit is adapted to configure the stimulating current to change the level of the at least one NO synthase of the heart tissue by an amount sufficient to treat heart failure of the subject.

For some applications, the control unit is adapted to configure the stimulating current to change the level of the at least one NO synthase of the heart tissue by an amount sufficient to treat atrial fibrillation of the subject.

For some applications, the control unit is adapted to configure the stimulating current to change the level of the at least one NO synthase of the heart tissue by an amount sufficient to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is still further provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to change a physiological parameter of the subject selected from the list consisting of: a hemodynamic parameter, and a cardiac geometry parameter, sufficiently to treat a cardiac condition of the subject.

For some applications, the cardiac condition is selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock, and the control unit is adapted to configure the stimulating current to change the selected physiological parameter sufficiently to treat the selected cardiac condition.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is yet further provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to change a myocardial cellular anatomy parameter of the subject sufficiently to treat a cardiac condition of the subject.

For some applications, the cardiac condition is selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock, and the control unit is adapted to configure the stimulating current to change the myocardial cellular anatomy parameter sufficiently to treat the selected cardiac condition.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is also provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to suppress inflammation of the subject.

For some applications, the control unit is adapted to configure the stimulating current to suppress the inflammation sufficiently to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, cardiogenic shock, atrial fibrillation, and thromboembolism.

For some applications, the control unit is adapted to configure the stimulating current to suppress the inflammation sufficiently to treat a stimulation-treatable condition of the subject.

In an embodiment, the control unit is adapted to configure the stimulating current to change a level of an inflammatory marker selected from the list consisting of: tumor necrosis factor alpha, interleukin 6, activin A, transforming growth factor, interferon, interleukin 1 beta, interleukin 18, interleukin 12, and C-reactive protein. For some applications, the control unit is adapted to configure the stimulating current to change the level of the selected inflammatory marker sufficiently to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock. For some applications, the control unit is adapted to configure the stimulating current to change the level of the selected inflammatory marker sufficiently to treat a stimulation-treatable condition of the subject. For some applications, the control unit is adapted to configure the stimulating current to change the level of the selected inflammatory marker sufficiently to treat a portion of a body of the subject selected from the list consisting of: a heart, a brain, lungs, an organ of a respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex. For some applications, the control unit is adapted to configure the stimulating current to change the level of the selected inflammatory marker sufficiently to attenuate muscle contractility of the subject.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is further provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to change a level of a neurohormone peptide selected from the list consisting of: N-terminal pro-brain natriuretic peptide (NT-pro-BNP), and a catecholamine, sufficiently to treat a cardiac condition of the subject.

For some applications, the cardiac condition is selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock, and the control unit is adapted to configure the stimulating current to change the level of the selected neurohormone peptide sufficiently to treat the selected cardiac condition.

In an embodiment, the neurohormone peptide includes NT-pro-BNP, and the control unit is adapted to configure the stimulating current to change the level of NT-pro-BNP. For some applications, the control unit is adapted to configure the stimulating current to change the level of NT-pro-BNP by an amount sufficient to treat heart failure of the subject. For some applications, the control unit is adapted to configure the stimulating current to change the level of NT-pro-BNP by an amount sufficient to treat atrial fibrillation of the subject. For some applications, the control unit is adapted to apply the stimulating current during a period having a duration of at least one week.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is still further provided, in accordance with an embodiment of the present invention, apparatus for treating a subject who has undergone a coronary artery bypass graft (CABG) procedure, including:

an electrode device, adapted to be coupled to parasympathetic nervous tissue of the subject; and a control unit, adapted to drive the electrode device to apply a stimulating current to the tissue, and to configure the stimulating current to suppress at least one of: post-CABG inflammation and post-CABG atrial fibrillation.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is yet further provided, in accordance with an embodiment of the present invention, apparatus for treating a subject suffering from atrial fibrillation, including:

an electrical cardioversion device;

an electrode device, adapted to be coupled to parasympathetic nervous tissue of the subject; and a control unit, adapted to drive the electrode device to apply a stimulating current to the tissue, and to configure the stimulating current to suppress inflammation of the subject, and, thereafter, drive the cardioversion device to apply cardioversion treatment to the subject.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is also provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to inhibit release of a proinflammatory cytokine.

For some applications, the control unit is adapted to configure the stimulating current to inhibit the release of the proinflammatory cytokine sufficiently to treat heart failure of the subject. For some applications, the control unit is adapted to configure the stimulating current to inhibit the release of the proinflammatory cytokine sufficiently to treat atrial fibrillation of the subject.

For some applications, the control unit is adapted to apply the stimulating current during a period having a duration of at least one week. For some applications, the control unit is adapted to configure the stimulating current to inhibit the release of the proinflammatory cytokine sufficiently to treat a cardiac condition of the subject selected from the list consisting of: heart failure, congestive heart failure, diastolic heart failure, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock. For some applications, the control unit is adapted to configure the stimulating current to inhibit the release of the proinflammatory cytokine sufficiently to treat a stimulation-treatable condition of the subject.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is additionally provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to inhibit release of C-reactive protein.

For some applications, the control unit is adapted to configure the stimulating current to inhibit the release of the C-reactive protein sufficiently to treat heart failure of the subject. For some applications, the control unit is adapted to configure the stimulating current to inhibit the release of the C-reactive protein sufficiently to treat atrial fibrillation of the subject.

For some applications, the control unit is adapted to apply the stimulating current during a period having a duration of at least one week.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is yet additionally provided, in accordance with an embodiment of the present invention, apparatus for treating a subject, including:

an electrode device, adapted to be coupled to parasympathetic nervous tissue of the subject; and a control unit, adapted to drive the electrode device to apply a stimulating current to the tissue, and to configure the stimulating current to change a level of Connexin 43.

For some applications, the control unit is adapted to configure the stimulating current to change the level of Connexin 43 by an amount sufficient to treat a cardiac condition of the subject selected from the list consisting of: heart failure, congestive heart failure, diastolic heart failure, atrial fibrillation, angina, cardiac arrest, arrhythmia, myocardial infarction, hypertension, endocarditis, myocarditis, atherosclerosis, restenosis, cardiomyopathy, post-myocardial infarct remodeling, arteritis, thrombophlebitis, pericarditis, myocardial ischemia, sick sinus syndrome, and cardiogenic shock.

For some applications, the control unit is adapted to configure the stimulating current to change the level of Connexin 43 by an amount sufficient to treat a portion of a body of the subject selected from the list consisting of: a heart, a brain, lungs, an organ of a respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex.

For some applications, the control unit is adapted to configure the stimulating current to change the level of Connexin 43 by an amount sufficient to treat a condition of the subject selected from the list consisting of: tuberous sclerosis, breast cancer, carcinomas, melanoma, osteoarthritis, a wound, a seizure, bladder overactivity, bladder outlet obstruction, Huntington's disease, and Alzheimer's disease.

For some applications, the control unit is adapted to apply the stimulating current during a period having a duration of at least one week.

In an embodiment, the parasympathetic tissue includes a vagus nerve of the subject, and the electrode device is adapted to be coupled to the vagus nerve. Alternatively, the parasympathetic tissue includes an epicardial fat pad of the subject, and the electrode device is adapted to be coupled to the epicardial fat pad. Further alternatively, the parasympathetic tissue is selected from the list consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and the electrode device is adapted to be coupled to the selected parasympathetic tissue.

There is still additionally provided, in accordance with an embodiment of the present invention, a method for treating a condition of a subject, including:

identifying a clinical benefit for the subject to experience a change in a level of at least one NO synthase of the subject selected from the list consisting of: NOS-1, NOS-2, and NOS-3;

applying a stimulating current to parasympathetic nervous tissue of the subject; and configuring the stimulating current to change the level of the at least one NO synthase.

There is yet additionally provided, in accordance with an embodiment of the present invention, a method for treating a subject, including:

identifying a clinical benefit for the subject to experience a change in a physiological parameter of the subject selected from the list consisting of: a hemodynamic parameter, and a cardiac geometry parameter;

applying a stimulating current to parasympathetic nervous tissue of the subject; and configuring the stimulating current to change the selected physiological parameter sufficiently to treat a cardiac condition of the subject.

There is still additionally provided, in accordance with an embodiment of the present invention, a method for treating a subject, including:

identifying a clinical benefit for the subject to experience a change in a myocardial cellular anatomy parameter of the subject;

applying a stimulating current to parasympathetic nervous tissue of the subject; and configuring the stimulating current to change the myocardial cellular anatomy parameter sufficiently to treat a cardiac condition of the subject.

There is yet additionally provided, in accordance with an embodiment of the present invention, a method for treating a subject, including:

identifying a clinical benefit for the subject to experience a suppression of inflammation of the subject;

applying a stimulating current to parasympathetic nervous tissue of the subject; and configuring the stimulating current to suppress the inflammation.

There is also provided, in accordance with an embodiment of the present invention, a method for treating a subject, including:

identifying a clinical benefit for the subject to experience a change in a level of a neurohormone peptide selected from the list consisting of: N-terminal pro-brain natriuretic peptide (NT-pro-BNP), and a catecholamine;

applying a stimulating current to parasympathetic nervous tissue of the subject; and configuring the stimulating current to change the level of the selected neurohormone peptide sufficiently to treat a cardiac condition of the subject.

There is further provided, in accordance with an embodiment of the present invention, a method including:

selecting a subject who has undergone a coronary artery bypass graft (CABG) procedure;

applying a stimulating current to parasympathetic nervous tissue of the subject; and configuring the stimulating current to suppress at least one of: post-CABG inflammation and post-CABG atrial fibrillation.

There is still further provided, in accordance with an embodiment of the present invention, a method including:

selecting a subject suffering from atrial fibrillation;

applying a stimulating current to parasympathetic nervous tissue of the subject;

configuring the stimulating current to suppress inflammation of the subject; and after applying and configuring the stimulating current, applying electrical cardioversion treatment to the subject.

There is additionally provided, in accordance with an embodiment of the present invention, a method for treating a subject, including:

identifying a clinical benefit for the subject to experience inhibition of release of a proinflammatory cytokine;

applying a stimulating current to parasympathetic nervous tissue of the subject; and configuring the stimulating current to inhibit release of the proinflammatory cytokine.

There is yet additionally provided, in accordance with an embodiment of the present invention, a method for treating a subject, including:

identifying a clinical benefit for the subject to experience inhibition of release of C-reactive protein;

applying a stimulating current to parasympathetic nervous tissue of the subject; and configuring the stimulating current to inhibit release of the C-reactive protein.

There is still additionally provided, in accordance with an embodiment of the present invention, a method for treating a subject, including:

identifying a clinical benefit for the subject to experience a change in a level of Connexin 43;

applying a stimulating current to parasympathetic nervous tissue of the subject; and configuring the stimulating current to change the level of Connexin 43.

The present invention will be more fully understood from the following detailed description of an embodiments thereof, taken together with the drawings, in which:

BRIEF DESCRIPTION OF THE DRAWINGS

FIGS. 7 and 8 are tables showing hemodynamic, angiographic, echocardiographic, and Doppler measurements made during an in vivo experiment conducted on 19 dogs, measured in accordance with an embodiment of the present invention;

FIG. 9 is a table showing histomorphometric measurements made during the experiment of FIGS. 7 and 8, measured in accordance with an embodiment of the present invention;

DETAILED DESCRIPTION OF EMBODIMENTS

Figure 1:
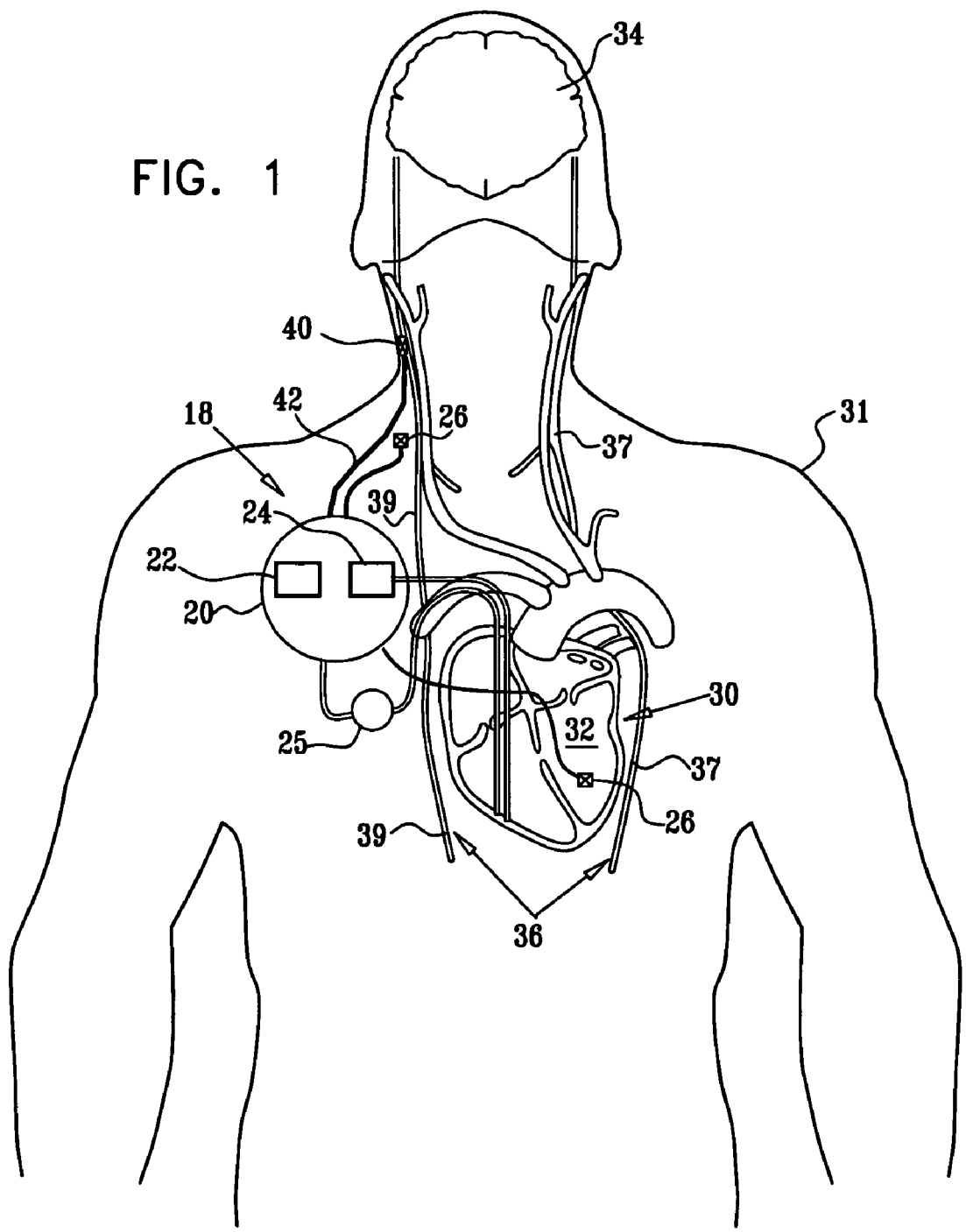
FIG. 1 is a block diagram that schematically illustrates a vagal stimulation system applied to a vagus nerve of a patient, in accordance with an embodiment of the present invention.

FIG. 1 is a block diagram that schematically illustrates a vagal stimulation system 18 comprising a multipolar electrode device 40, in accordance with an embodiment of the present invention. Electrode device 40 is applied to a portion of a vagus nerve 36 (either a left vagus nerve 37 or a right vagus nerve 39), which innervates a heart 30 of a patient 31. Typically, system 18 is utilized for treating a heart condition such as heart failure and/or cardiac arrhythmia. Vagal stimulation system 18 further comprises an implanted or external control unit 20, which typically communicates with electrode device 40 over a set of leads 42. For some applications, control unit 20 drives electrode device 40 to (i) apply signals to induce the propagation of efferent nerve impulses towards heart 30, and (ii) suppress artificially-induced afferent nerve impulses towards a brain 34 of the patient, in order to minimize unintended side effects of the signal application. Alternatively, control unit 20 drives electrode device 40 to apply signals that induce symmetric or asymmetric bi-directional propagation of nerve impulses. For some applications, the efferent nerve pulses in vagus nerve 36 are induced by electrode device 40 in order to regulate the heart rate of the patient.

For some applications, control unit 20 is adapted to receive feedback from one or more of the electrodes in electrode device 40, and to regulate the signals applied to the electrode device responsive thereto.

Control unit 20 is typically adapted to receive and analyze one or more sensed physiological parameters or other parameters of the patient, such as heart rate, electrocardiogram (ECG), blood pressure, indicators of decreased cardiac contractility, cardiac output, norepinephrine concentration, or motion of the patient. In order to receive these sensed parameters, control unit 20 may comprise, for example, an ECG monitor 24, connected to a site on the patient's body such as heart 30, for example using one or more subcutaneous sensors or ventricular and/or atrial intracardiac sensors. The control unit may also comprise an accelerometer 22 for detecting motion of the patient. Alternatively, ECG monitor 24 and/or accelerometer 22 comprise separate implanted devices placed external to control unit 20, and, optionally, external to the patient's body. Alternatively or additionally, control unit 20 receives signals from one or more physiological sensors 26, such as blood pressure sensors. Sensors 26 are typically implanted in the patient, for example in a left ventricle 32 of heart 30. In an embodiment, control unit 20 comprises or is coupled to an implanted device 25 for monitoring and correcting the heart rate, such as an implantable cardioverter defibrillator (ICD) or a pacemaker (e.g., a bi-ventricular or standard pacemaker). For example, implanted device 25 may be incorporated into a control loop executed by control unit 20, in order to increase the heart rate when the heart rate for any reason is too low.

Figure 2A:
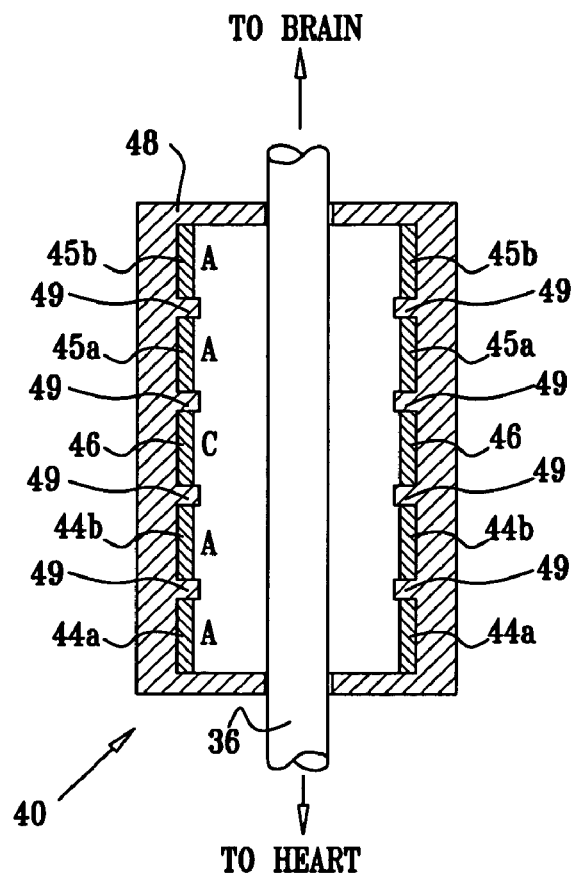
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 40 applied to vagus nerve 36, in accordance with an embodiment of the present invention. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Typically, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 46 is regulated, whereupon more anodal current is driven through the one or more anodes having lower relative impedance. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Figure 2B:
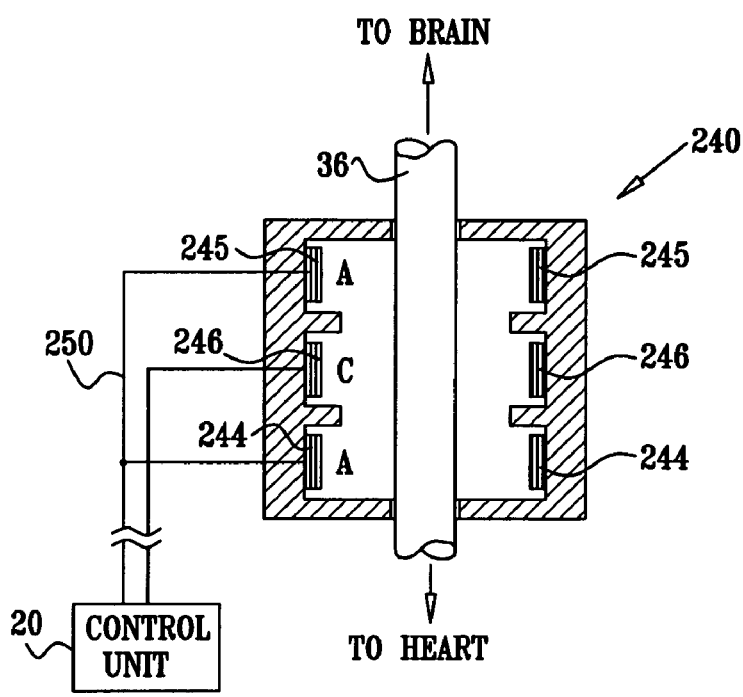
FIG. 2B is a simplified cross-sectional illustration of a generally-cylindrical electrode device applied to a vagus nerve, in accordance with an embodiment of the present invention.

Reference is now made to FIG. 2B, which is a simplified cross-sectional illustration of a generally-cylindrical electrode device 240 applied to vagus nerve 36, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 2A. Cathodes 46 and anode sets 44 and 45 (collectively, "electrodes") are typically mounted in an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 36. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). For some applications, the distance between the ends of protrusions 49 and the center of the vagus nerve is between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 40.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is typically positioned in cuff 48 to apply current at the location on vagus nerve 36 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

As appropriate, techniques described herein are practiced in conjunction with methods and apparatus described in U.S. patent application Ser. No. 10/205,474 to Gross et al., filed Jul. 24, 2002, entitled, "Electrode assembly for nerve control," which published as US Patent Application Publication 2003/0050677, is assigned to the assignee of the present patent application, and is incorporated herein by reference. Alternatively or additionally, techniques described herein are practiced in conjunction with methods and apparatus described in U.S. patent application Ser. No. 10/205,475 to Gross et al., filed Jul. 24, 2002, entitled, "Selective nerve fiber stimulation for treating heart conditions," which published as US Patent Application Publication 2003/0045909, is assigned to the assignee of the present patent application, and is incorporated herein by reference. Further alternatively or additionally, techniques described herein are practiced in conjunction with methods and apparatus described in U.S. Provisional Patent Application 60/383,157 to Ayal et al., filed May 23, 2002, entitled, "Inverse recruitment for autonomic nerve systems," which is assigned to the assignee of the present patent application and is incorporated herein by reference.

Figure 2C:
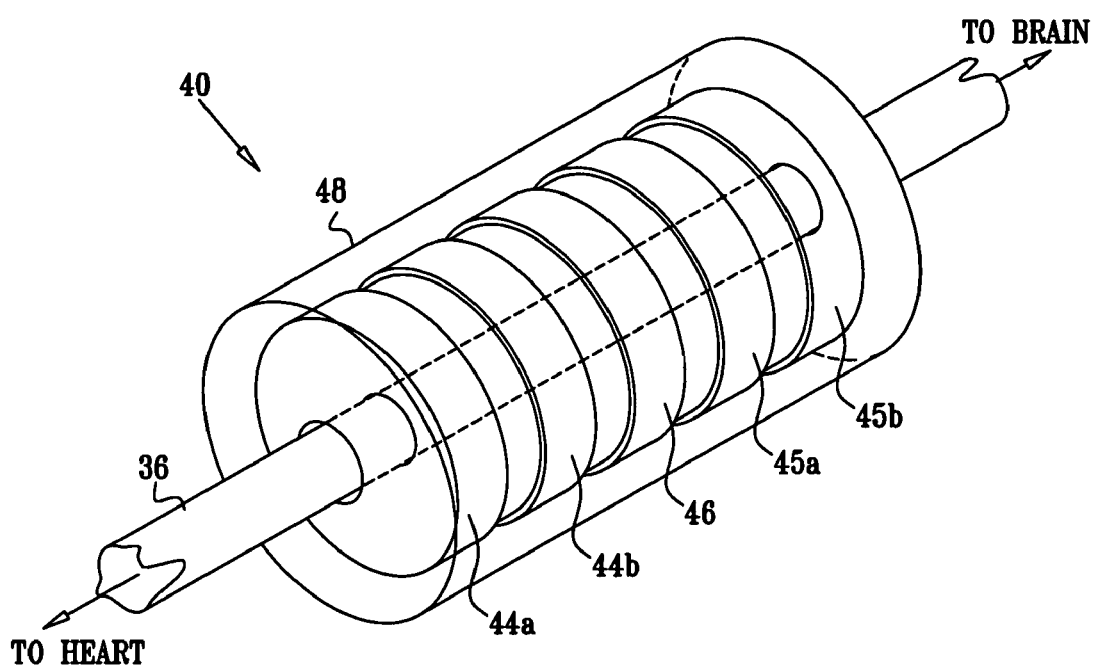
FIG. 2C is a simplified perspective illustration of the electrode device of FIG. 2A, in accordance with an embodiment of the present invention.

FIG. 2C is a simplified perspective illustration of electrode device 40 (FIG. 2A), in accordance with an embodiment of the present invention. When applied to vagus nerve 36, electrode device 40 typically encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes typically comprise ring electrodes adapted to apply a generally uniform current around the circumference of the nerve, as best shown in FIG. 2C.

Figure 3:
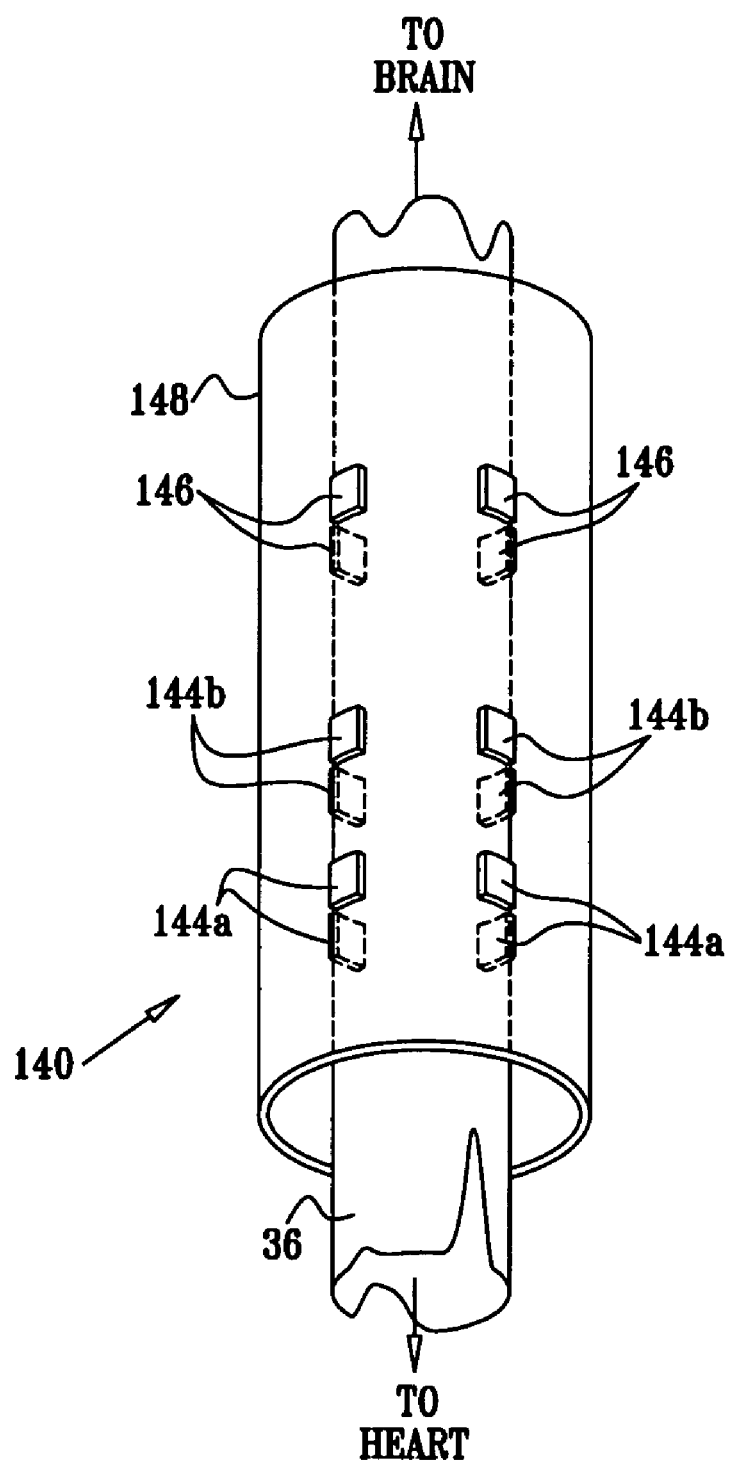
FIG. 3 is a simplified perspective illustration of a multipolar point electrode device applied to a vagus nerve, in accordance with an embodiment of the present invention.

FIG. 3 is a simplified perspective illustration of a multipolar point electrode device 140 applied to vagus nerve 36, in accordance with an embodiment of the present invention. In this embodiment, anodes 144a and 144b and a cathode 146 typically comprise point electrodes (typically 2 to 100), fixed inside an insulating cuff 148 and arranged around vagus nerve 36 so as to selectively stimulate nerve fibers according to their positions inside the nerve. In this case, techniques described in the above-cited articles by Grill et al., Goodall et al., and/or Veraart et al. are typically used. The point electrodes typically have a surface area between about 0.01 mm² and 1 mm². In some applications, the point electrodes are in contact with vagus nerve 36, as shown, while in other applications the point electrodes are recessed in cuff 148, so as not to come in direct contact with vagus nerve 36, similar to the recessed ring electrode arrangement described above with reference to FIG. 2A. For some applications, one or more of the electrodes, such as cathode 146 or anode 144a, comprise a ring electrode, as described with reference to FIG. 2C, such that electrode device 140 comprises both ring electrode(s) and point electrodes (configuration not shown). Additionally, electrode device 40 optionally comprises an afferent anode set (positioned like anodes 45a and 45b in FIG. 2A), the anodes of which comprise point electrodes and/or ring electrodes.

Alternatively, ordinary, non-cuff electrodes are used, such as when the electrodes are placed on the epicardial fat pads instead of on the vagus nerve.

Figure 4:
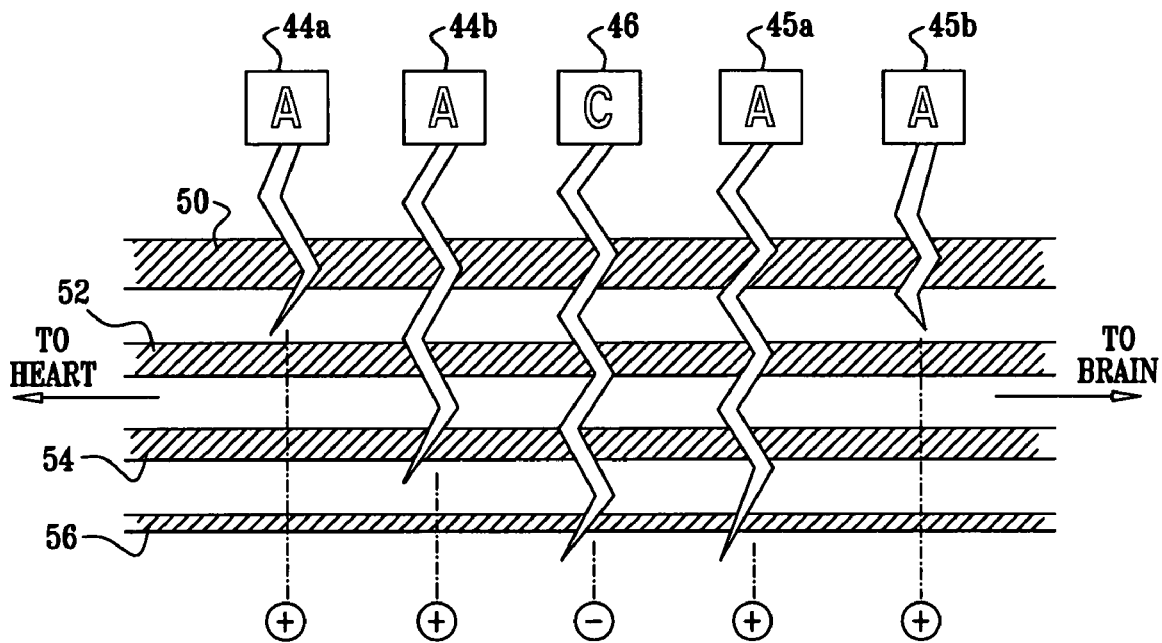
FIG. 4 is a conceptual illustration of the application of current to a vagus nerve, in accordance with an embodiment of the present invention.

FIG. 4 is a conceptual illustration of the application of current to vagus nerve 36 in order to achieve smaller-to-larger diameter fiber recruitment, in accordance with an embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 4 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 36.

In order to suppress artificially-induced afferent action potentials from traveling towards the brain in response to the cathodic stimulation, control unit 20 typically drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

In an embodiment of the present invention, stimulation of the vagus nerve is applied responsive to one or more sensed parameters. Control unit 20 is typically configured to commence or halt stimulation, or to vary the amount and/or timing of stimulation in order to achieve a desired target heart rate, typically based on configuration values and on parameters including one or more of the following:

Heart rate—the control unit can be configured to drive electrode device 40 to stimulate the vagus nerve only when the heart rate exceeds a certain value.

ECG readings—the control unit can be configured to drive electrode device 40 to stimulate the vagus nerve based on certain ECG readings, such as readings indicative of designated forms of arrhythmia. Additionally, ECG readings are typically used for achieving a desire heart rate, as described below with reference to FIG. 5.

Blood pressure—the control unit can be configured to regulate the current applied by electrode device 40 to the vagus nerve when blood pressure exceeds a certain threshold or falls below a certain threshold.

Indicators of decreased cardiac contractility—these indicators include left ventricular pressure (LVP). When LVP and/or d(LVP)/dt exceeds a certain threshold or falls below a certain threshold, control unit 20 can drive electrode device 40 to regulate the current applied by electrode device 40 to the vagus nerve.

Motion of the patient—the control unit can be configured to interpret motion of the patient as an indicator of increased exertion by the patient, and appropriately reduce parasympathetic stimulation of the heart in order to allow the heart to naturally increase its rate.

Heart rate variability—the control unit can be configured to drive electrode device 40 to stimulate the vagus nerve based on heart rate variability, which is typically calculated based on certain ECG readings.

Norepinephrine concentration—the control unit can be configured to drive electrode device 40 to stimulate the vagus nerve based on norepinephrine concentration.

Cardiac output—the control unit can be configured to drive electrode device 40 to stimulate the vagus nerve based on cardiac output, which is typically determined using impedance cardiography.

Baroreflex sensitivity—the control unit can be configured to drive electrode device 40 to stimulate the vagus nerve based on baroreflex sensitivity.

The parameters and behaviors included in this list are for illustrative purposes only, and other possible parameters and/or behaviors will readily present themselves to those skilled in the art, having read the disclosure of the present patent application.

In an embodiment of the present invention, control unit 20 is configured to drive electrode device 40 to stimulate the vagus nerve so as to reduce the heart rate of the subject towards a target heart rate. The target heart rate is typically (a) programmable or configurable, (b) determined responsive to one or more sensed physiological values, such as those described hereinabove (e.g., motion, blood pressure, etc.), and/or (c) determined responsive to a time of day or circadian cycle of the subject. Parameters of stimulation are varied in real time in order to vary the heart-rate-lowering effects of the stimulation. For example, such parameters may include the amplitude of the applied current. Alternatively or additionally, in an embodiment of the present invention, the stimulation is applied in a series of pulses that are synchronized or are not synchronized with the cardiac cycle of the subject, such as described hereinbelow with reference to FIG. 5. Parameters of such pulse series typically include, but are not limited to:

Timing of the stimulation within the cardiac cycle. Delivery of the series of pulses typically begins after a fixed or variable delay following an ECG feature, such as each R- or P-wave. For some applications, the delay is between about 20 ms and about 300 ms from the R-wave, or between about 100 and about 500 ms from the P-wave.

Pulse duration (width). Longer pulse durations typically result in a greater heart-rate-lowering effect. For some applications, the pulse duration is between about 0.2 and about 4 ms.

Pulse repetition interval. Maintaining a pulse repetition interval (the time from the initiation of a pulse to the initiation of the following pulse) greater than about 3 ms generally results in maximal stimulation effectiveness for multiple pulses within a burst.

Pulses per trigger (PPT). A greater PPT (the number of pulses in each series of pulses after a trigger such as an R-wave) typically results in a greater heart-rate-lowering effect. For some applications, PPT is between about 0 and about 8.

Amplitude. A greater amplitude of the signal applied typically results in a greater heart-rate-lowering effect. The amplitude is typically less than about 10 milliamps, e.g., between about 2 and about 10 milliamps. For some applications, the amplitude is between about 2 and about 6 milliamps.

Duty cycle. Application of stimulation every heartbeat typically results in a greater heart-rate-lowering effect. For less heart rate reduction, stimulation is applied only once every several heartbeats.

Choice of vagus nerve. Stimulation of the right vagus nerve typically results in greater heart rate reduction than stimulation of the left vagus nerve.

"On"/"off" ratio and timing. For some applications, the device operates intermittently, alternating between "on" and "off" states, the length of each state typically between 0 and about 300 seconds (with a 0-length "off" state equivalent to always "on"). Greater heart rate reduction is typically achieved if the device is "on" a greater portion of the time.

For some applications, values of the "on"/"off" parameter are determined in real time, responsive to one or more inputs, such as sensed physiological values. Such inputs typically include motion or activity of the subject (e.g., detected using an accelerometer), the average heart rate of the subject when the device is in "off" mode, and/or the time of day. For example, the device may operate in continuous "on" mode when the subject is exercising and therefore has a high heart rate, and the device may alternate between "on" and "off" when the subject is at rest. As a result, the heart-rate-lowering effect is concentrated during periods of high heart rate, and the nerve is allowed to rest when the heart rate is generally naturally lower.

For some applications, heart rate regulation is achieved by setting two or more parameters in combination. For example, if it is desired to apply 5.2 pulses of stimulation, the control unit may apply 5 pulses of 1 ms duration each, followed by a single pulse of 0.2 ms duration. For other applications, the control unit switches between two values of PPT, so that the desired PPT is achieved by averaging the applied PPTs. For example, a sequence of PPTs may be 5, 5, 5, 5, 6, 5, 5, 5, 5, 6, . . . , in order to achieve an effective PPT of 5.2.

In an embodiment of the present invention, control unit 20 uses a slow-reacting heart rate regulation algorithm to modify heart-rate-controlling parameters of the stimulation, i.e., the algorithm varies stimulation parameters slowly in reaction to changes in heart rate. For example, in response to a sudden increase in heart rate, e.g., an increase from a target heart rate of 60 beats per minute (BPM) to 100 BPM over a period of only a few seconds, the algorithm slowly increases the stimulation level over a period of minutes. If the heart rate naturally returns to the target rate over this period, the stimulation levels generally do not change substantially before returning to baseline levels.

For example, the heart of a subject is regulated while the subject is inactive, such as while sitting. When the subject suddenly increases his activity level, such as by standing up or climbing stairs, the subject's heart rate increases suddenly. In response, the control unit adjusts the stimulation parameters slowly to reduce the subject's heart rate. Such a gradual modification of stimulation parameters allows the subject to engage in relatively stressful activities for a short period of time before his heart rate is substantially regulated, generally resulting in an improved quality of life.

In an embodiment of the present invention, control unit 20 is adapted to detect bradycardia (i.e., that an average detected R-R interval exceeds a preset bradycardia limit), and to terminate heart rate regulation substantially immediately upon such detection, such as by ceasing vagal stimulation. Alternatively or additionally, the control unit uses an algorithm that reacts quickly to regulate heart rate when the heart rate crosses limits that are predefined (e.g., a low limit of 40 beats per minute (BPM) and a high limit of 140 BPM), or determined in real time, such as responsive to sensed physiological values.

In an embodiment of the present invention, control unit 20 is configured to operate intermittently. Typically, upon each resumption of operation, control unit 20 sets the stimulation parameters to those in effect immediately prior to the most recent cessation of operation. For some applications, such parameters applied upon resumption of operation are maintained without adjustment for a certain number of heartbeats (e.g., between about one and about ten), in order to allow the heart rate to stabilize after resumption of operation.

For some applications, control unit 20 is configured to operate intermittently with gradual changes in stimulation. For example, the control unit may operate according to the following "on"/"off" pattern: (a) "off" mode for 30 minutes, (b) a two-minute "on" period characterized by a gradual increase in stimulation so as to achieve a target heart rate, (c) a six-minute "on" period of feedback-controlled stimulation to maintain the target heart rate, and (d) a two-minute "on" period characterized by a gradual decrease in stimulation to return the heart rate to baseline. The control unit then repeats the cycle, beginning with another 30-minute "off" period.

In an embodiment of the present invention, control unit 20 is configured to operate in an adaptive intermittent mode. The control unit sets the target heart rate for the "on" period equal to a fixed or configurable fraction of the average heart rate during the previous "off" period, typically bounded by a preset minimum. For example, assume that for a certain subject the average heart rates during sleep and during exercise are 70 and 150 BPM, respectively. Further assume that the target heart rate for the "on" period is set at 70% of the average heart rate during the previous "off" period, with a minimum of 60 BPM. During sleep, stimulation is applied so as to produce a heart rate of MAX(60 BPM, 70% of 70 BPM)=60 BPM, and is thus applied with parameters similar to those that would be used in the simple intermittent mode described hereinabove. Correspondingly, during exercise, stimulation is applied so as to produce a heart rate of MAX(60 BPM, 70% of 150 BPM)=105 BPM.

In an embodiment of the present invention, a heart rate regulation algorithm used by control unit 20 has as an input a time derivative of the sensed heart rate. The algorithm typically directs the control unit to respond slowly to increases in heart rate and quickly to decreases in heart rate.

In an embodiment of the present invention, the heart rate regulation algorithm utilizes sensed physiological parameters for feedback. For some applications, the feedback is updated periodically by inputting the current heart rate. For some applications, such updating occurs at equally-spaced intervals. Alternatively, the feedback is updated by inputting the current heart rate upon each detection of a feature of the ECG, such as an R-wave. In order to convert non-fixed R-R intervals into a form similar to canonical fixed intervals, the algorithm adds the square of each R-R interval, thus taking into account the non-uniformity of the update interval, e.g., in order to properly analyze feedback stability using standard tools and methods developed for canonical feedback.

In an embodiment of the present invention, control unit 20 implements a detection blanking period, during which the control unit does not detect heart beats. In some instances, such non-detection may reduce false detections of heart beats. One or both of the following techniques are typically implemented:

Absolute blanking. An expected maximal heart rate is used to determine a minimum interval between expected heart beats. During this interval, the control unit does not detect heart beats, thereby generally reducing false detections. For example, the expected maximal heart rate may be 200 BPM, resulting in a minimal detection interval of 300 milliseconds. After detection of a beat, the control unit disregards any signals indicative of a beat during the next 300 milliseconds.

Stimulation blanking. During application of a stimulation burst, and for an interval thereafter, the control unit does not detect heart beats, thereby generally reducing false detections of stimulation artifacts as beats. For example, assume stimulation is applied with the following parameters: a PPT of 5 pulses, a pulse width of 1 ms, and a pulse repetition interval of 5 ms. The control unit disregards any signals indicative of a beat during the entire 25 ms duration of the burst and for an additional interval thereafter, e.g., 50 ms, resulting in a total blanking period of 75 ms beginning with the start of the burst.

In an embodiment of the present invention, the heart rate regulation algorithm is implemented using only integer arithmetic. For example, division is implemented as integer division by a power of two, and multiplication is always of two 8-bit numbers. For some applications, time is measured in units of 1/128 of a second.

In an embodiment of the present invention, control unit 20 implements an integral feedback controller, which can most generally be described by:

$$K = K_I * \int e \, dt$$

in which K represents the strength of the feedback, $K_I$ is a coefficient, and $\int e \, dt$ represents the cumulative error. It is to be understood that such an integral feedback controller can be implemented in hardware, or in software running in control unit 20.

In an embodiment of such an integral controller, heart rate is typically expressed as an R-R interval (the inverse of heart rate). Parameters of the integral controller typically include TargetRR (the target R-R interval) and TimeCoeff (which determines the overall feedback reaction time).

Typically, following the detection of each R-wave, the previous R-R interval is calculated and assigned to a variable (LastRR). e (i.e., the difference between the target R-R interval and the last measured R-R interval) is then calculated as:

$$e = \text{Target}RR - \text{Last}RR$$

e is typically limited by control unit 20 to a certain range, such as between −0.25 and +0.25 seconds, by reducing values outside the range to the endpoint values of the range. Similarly, LastRR is typically limited, such as to $^{255}/_{128}$ seconds. The error is then calculated by multiplying LastRR by e:

$$\text{Error} = e * \text{Last}RR$$

A cumulative error (representing the integral in the above generalized equation) is then calculated by dividing the error by TimeCoeff and adding the result to the cumulative error, as follows:

$$\text{Integral} = \text{Integral} + \text{Error}/2^{\text{TimeCoeff}}$$

The integral is limited to positive values less than, e.g., 36,863. The number of pulses applied in the next series of pulses (pulses per trigger, or PPT) is equal to the integral/4096.

The following table illustrates example calculations using a heart rate regulation algorithm that implements an integral controller, in accordance with an embodiment of the present invention. In this example, the parameter TargetRR (the target heart rate) is set to 1 second ($^{128}/_{128}$ seconds), and the parameter TimeCoeff is set to 0. The initial value of Integral is 0. As can be seen in the table, the number of pulses per trigger (PPT) increases from 0 during the first heart beat, to 2 during the fourth heart beat of the example.

|  | Heart Beat Number | | | |
| --- | --- | --- | --- | --- |
|  | 1 | 2 | 3 | 4 |
| Heart rate (BPM) | 100 | 98 | 96 | 102 |
| R—R interval (ms) | 600 | 610 | 620 | 590 |
| R—R (1/128 sec) | 76 | 78 | 79 | 75 |
| e (1/128 sec) | 52 | 50 | 49 | 53 |
| Limited e | 32 | 32 | 32 | 32 |
| Error | 2432 | 2496 | 2528 | 2400 |
| Integral | 2432 | 4928 | 7456 | 9856 |
| PPT | 0 | 1 | 1 | 2 |

In an embodiment of the present invention, the heart rate regulation algorithm corrects for missed heart beats (either of physiological origin or because of a failure to detect a beat). Typically, to perform this correction, any R-R interval which is about twice as long as the immediately preceding R-R interval is interpreted as two R-R intervals, each having a length equal to half the measured interval. For example, the R-R interval sequence (measured in seconds) 1, 1, 1, 2.2 is interpreted by the algorithm as the sequence 1, 1, 1, 1.1, 1.1. Alternatively or additionally, the algorithm corrects for premature beats, typically by adjusting the timing of beats that do not occur approximately halfway between the preceding and following beats. For example, the R-R interval sequence (measured in seconds) 1, 1, 0.5, 1.5 is interpreted as 1, 1, 1, 1, using the assumption that the third beat was premature.

In an embodiment of the present invention, control unit 20 is configured to operate in one of the following modes:

vagal stimulation is not applied when the heart rate of the subject is lower than the low end of the normal range of a heart rate of the subject and/or of a typical human subject;

vagal stimulation is not applied when the heart rate of the subject is lower than a threshold value equal to the current low end of the range of the heart rate of the subject, i.e., the threshold value is variable over time as the low end generally decreases as a result of chronic vagal stimulation treatment;

vagal stimulation is applied only when the heart rate of the subject is within the normal of range of a heart rate of the subject and/or of a typical human subjects;

vagal stimulation is applied only when the heart rate of the subject is greater than a programmable threshold value, such as a rate higher than a normal rate of the subject and/or a normal rate of a typical human subject. This mode generally removes peaks in heart rate; or vagal stimulation is applied using fixed programmable parameters, i.e., not in response to any feedback, target heart rate, or target heart rate range. These parameters may be externally updated from time to time, for example by a physician.

In an embodiment of the present invention, the amplitude of the applied stimulation current is calibrated by fixing a number of pulses in the series of pulses (per cardiac cycle), and then increasing the applied current until a desired predetermined heart rate reduction is achieved. Alternatively, the current is calibrated by fixing the number of pulses per series of pulses, and then increasing the current to achieve a substantial reduction in heart rate, e.g., 40%.

In embodiments of the present invention in which vagal stimulation system 18 comprises implanted device 25 for monitoring and correcting the heart rate, control unit 20 typically uses measured parameters received from device 25 as additional inputs for determining the level and/or type of stimulation to apply. Control unit 20 typically coordinates its behavior with the behavior of device 25. Control unit 20 and device 25 typically share sensors 26 in order to avoid redundancy in the combined system.

Optionally, vagal stimulation system 18 comprises a patient override, such as a switch that can be activated by the patient using an external magnet. The override typically can be used by the patient to activate vagal stimulation, for example in the event of arrhythmia apparently undetected by the system, or to deactivate vagal stimulation, for example in the event of apparently undetected physical exertion.

Figure 5:
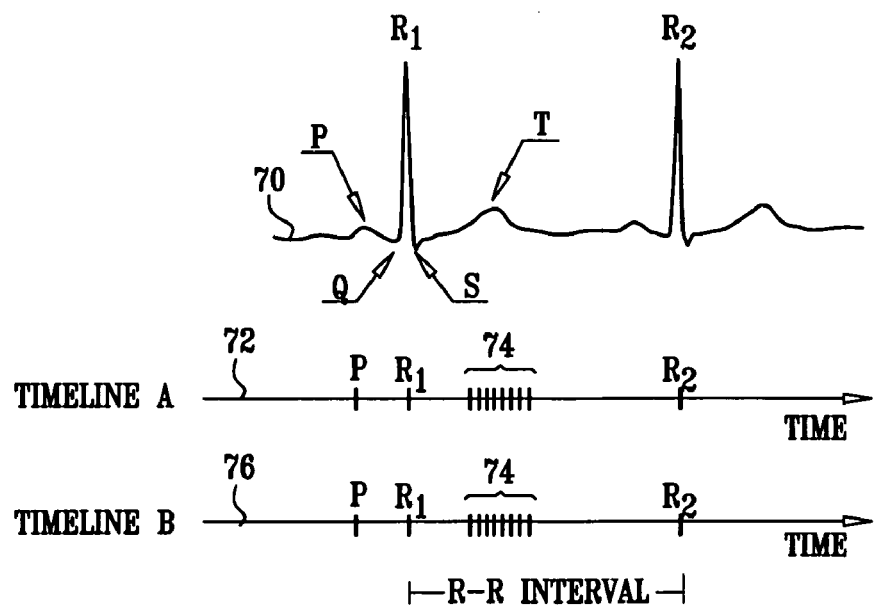
FIG. 5 is a simplified illustration of an electrocardiogram (ECG) recording and of example timelines showing the timing of the application of a series of stimulation pulses, in accordance with an embodiment of the present invention.

FIG. 5 is a simplified illustration of an ECG recording 70 and example timelines 72 and 76 showing the timing of the application of a burst of stimulation pulses 74, in accordance with an embodiment of the present invention. Stimulation is typically applied to vagus nerve 36 in a closed-loop system in order to achieve and maintain the desired target heart rate, determined as described above. Precise graded slowing of the heart beat is typically achieved by varying the number of nerve fibers stimulated, in a smaller-to-larger diameter order, and/or the intensity of vagus nerve stimulation, such as by changing the stimulation amplitude, pulse width, PPT, and/or delay. Stimulation with blocking, as described herein, is typically applied during each cardiac cycle in burst of pulses 74, typically containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

In an embodiment of the present invention (e.g., when the heart rate regulation algorithm described hereinabove is not implemented), to apply the closed-loop system, the target heart rate is expressed as a ventricular R-R interval (shown as the interval between $R_1$ and $R_2$ in FIG. 5). The actual R-R interval is measured in real time and compared with the target R-R interval. The difference between the two intervals is defined as a control error. Control unit 20 calculates the change in stimulation necessary to move the actual R-R towards the target R-R, and drives electrode device 40 to apply the new calculated stimulation. Intermittently, e.g., every 1, 10, or 100 beats, measured R-R intervals or average R-R intervals are evaluated, and stimulation of the vagus nerve is modified accordingly.

In an embodiment, vagal stimulation system 18 is further configured to apply stimulation responsive to pre-set time parameters, such as intermittently, constantly, or based on the time of day.

Alternatively or additionally, one or more of the techniques of smaller-to-larger diameter fiber recruitment, selective fiber population stimulation and blocking, and varying the intensity of vagus nerve stimulation by changing the stimulation amplitude, pulse width, PPT, and/or delay, are applied in conjunction with methods and apparatus described in one or more of the patents, patent applications, articles and books cited herein.

In an embodiment of the present invention, control unit 20 is configured to stimulate vagus nerve 36 so as to suppress the adrenergic system, in order to treat a subject suffering from a heart condition. For example, such vagal stimulation may be applied for treating a subject suffering from heart failure. In heart failure, hyper-activation of the adrenergic system damages the heart. This damage causes further activation of the adrenergic system, resulting in a vicious cycle. High adrenergic tone is harmful because it often results in excessive release of angiotensin and epinephrine, which increase vascular resistance (blood pressure), reduce heart rest time (accelerated heart rate), and cause direct toxic damage to myocardial muscles through oxygen free radicals and DNA damage. Artificial stimulation of the vagus nerve causes a down regulation of the adrenergic system, with reduced release of catecholamines. The natural effects of vagal stimulation, applied using the techniques described herein, typically reduces the release of catecholamines in the heart, thereby lowering the adrenergic tone at its source.

In an embodiment of the present invention, control unit 20 is configured to stimulate vagus nerve 36 so as to modulate atrial and ventricular contractility, in order to treat a subject suffering from a heart condition. Vagal stimulation generally reduces both atrial and ventricular contractility (see, for example, the above-cited article by Levy M N et al., entitled "Parasympathetic Control of the Heart"). Vagal stimulation, using the techniques described herein, typically (a) reduces the contractility of the atria, thereby reducing the pressure in the venous system, and (b) reduces the ventricular contractile force of the atria, which may reduce oxygen consumption, such as in cases of ischemia. For some applications, vagal stimulation, as described herein, is applied in order to reduce the contractile force of the ventricles in cases of hypertrophic cardiopathy. The vagal stimulation is typically applied with a current of at least about 4 mA.

In an embodiment of the present invention, control unit 20 is configured to stimulate vagus nerve 36 so as to improve coronary blood flow, in order to treat a subject suffering from a heart condition. Improving coronary blood flow by administering acetylcholine is a well known technique. For example, during Percutaneous Transluminal Coronary Angioplasty (PTCA), when maximal coronary dilation is needed, direct infusion of acetylcholine is often used to dilate the coronary arteries (see, for example, the above-cited article by Feliciano L et al.). For some applications, the vagal stimulation techniques described herein are used to improve coronary blood flow in subjects suffering from myocardial ischemia, ischemic heart disease, heart failure, and/or variant angina (spastic coronary arteries). It is hypothesized that such vagal stimulation simulates the effect of acetylcholine administration.

In an embodiment of the present invention, control unit 20 is configured to drive electrode device 40 to stimulate vagus nerve 36 so as to modify heart rate variability of the subject. For some applications, control unit 20 is configured to apply the stimulation having a duty cycle, which typically produces heart rate variability at the corresponding frequency. For example, such duty cycles may be in the range of once per every several heartbeats. For other applications, control unit 20 is configured to apply generally continuous stimulation (e.g., in a manner that produces a prolonged reduced level of heart rate variability).

For some applications, control unit 20 synchronizes the stimulation with the cardiac cycle of the subject, while for other applications, the control unit does not synchronize the stimulation with the cardiac cycle. For example, the stimulation may be applied in a series of pulses that are not synchronized with the cardiac cycle of the subject. Alternatively, the stimulation may be applied in a series of pulses that are synchronized with the cardiac cycle of the subject, such as described hereinabove with reference to FIG. 5.

For some applications, control unit 20 is configured to apply stimulation with parameters selected to reduce heart rate variability, while for other applications parameters are selected that increase variability. For example, when the stimulation is applied as a series of pulses, values of parameters that reduce heart variability may include one or more of the following:

Timing of the stimulation within the cardiac cycle: a delay of between about 50 ms and about 150 ms from the R-wave, or between about 100 and about 500 ms from the P-wave.

Pulse duration (width) of between about 0.5 and about 1.5 ms.

Pulse repetition interval (the time from the initiation of a pulse to the initiation of the following pulse) of between about 2 and about 8 ms.

Pulses per trigger (PPT), e.g., pulses per cardiac cycle, of between about 0 and about 8.

Amplitude of between about 5 and about 10 milliamps.

For some applications, the parameters of the stimulation are selected to both reduce the heart rate of the subject and heart rate variability of the subject. For other applications, the parameters are selected to reduce heart rate variability while substantially not reducing the average heart rate of the subject. In this context, a non-substantial heart rate reduction may be less than about 10%. For some applications, to achieve such a reduction in variability without a reduction in average rate, stimulation is applied using the feedback techniques described hereinabove, with a target heart rate greater than the normal average heart rate of the subject. Such stimulation typically does not substantially change the average heart rate, yet reduces heart rate variability (however, the instantaneous (but not average) heart rate may sometimes be reduced).

For some applications, in order to additionally reduce the heart rate, stimulation is applied using a target heart rate lower than the normal average heart rate of the subject. The magnitude of the change in average heart rate as well as the percentage of time during which reduced heart rate variability occurs in these applications are controlled by varying the difference between the target heart rate and the normal average heart rate.

For some applications, control unit 20 is configured to apply stimulation only when the subject is awake. Reducing heart variability when the subject is awake offsets natural increases in heart rate variability during this phase of the circadian cycle. Alternatively or additionally, control unit 20 is configured to apply or apply greater stimulation at times of exertion by the subject, in order to offset the increase in heart rate variability typically caused by exertion. For example, control unit 20 may determine that the subject is experiencing exertion responsive to an increase in heart rate, or responsive to a signal generated by an accelerometer. Alternatively, the control unit uses other techniques known in the art for detecting exertion.

In an embodiment of the present invention, control unit 20 is configured to drive electrode device 40 to stimulate vagus nerve 36 so as to modify heart rate variability in order to treat a condition of the subject. For some applications, the control unit is configured to additionally modify heart rate to treat the condition, while for other applications, the control unit is configured to modify heart rate variability while substantially not modifying average heart rate.

Therapeutic effects of reduction in heart rate variability include, but are not limited to:

Narrowing of the heart rate range, thereby eliminating very slow heart rates and very fast heart rates, both of which are inefficient for a subject suffering from heart failure. For this therapeutic application, control unit 20 is typically configured to reduce low-frequency heart rate variability, and to adjust the level of stimulation applied based on the circadian and activity cycles of the subject.

Stabilizing the heart rate, thereby reducing the occurrence of arrhythmia. For this therapeutic application, control unit 20 is typically configured to reduce heart rate variability at all frequencies.

Maximizing the mechanical efficiency of the heart by maintaining relatively constant ventricular filling times and pressures. For example, this therapeutic effect may be beneficial for subjects suffering from atrial fibrillation, in which fluctuations in heart filling times and pressure reduce cardiac efficiency.

Eliminating the normal cardiac response to changes in the breathing cycle (i.e., respiratory sinus arrhythmia). Although generally beneficial in young and efficient hearts, respiratory sinus arrhythmia may be harmful to subjects suffering from heart failure, because respiratory sinus arrhythmia causes unwanted accelerations and decelerations in the heart rate. For this therapeutic application, control unit 20 is typically configured to reduce heart rate variability at high frequencies.

Figure 6:
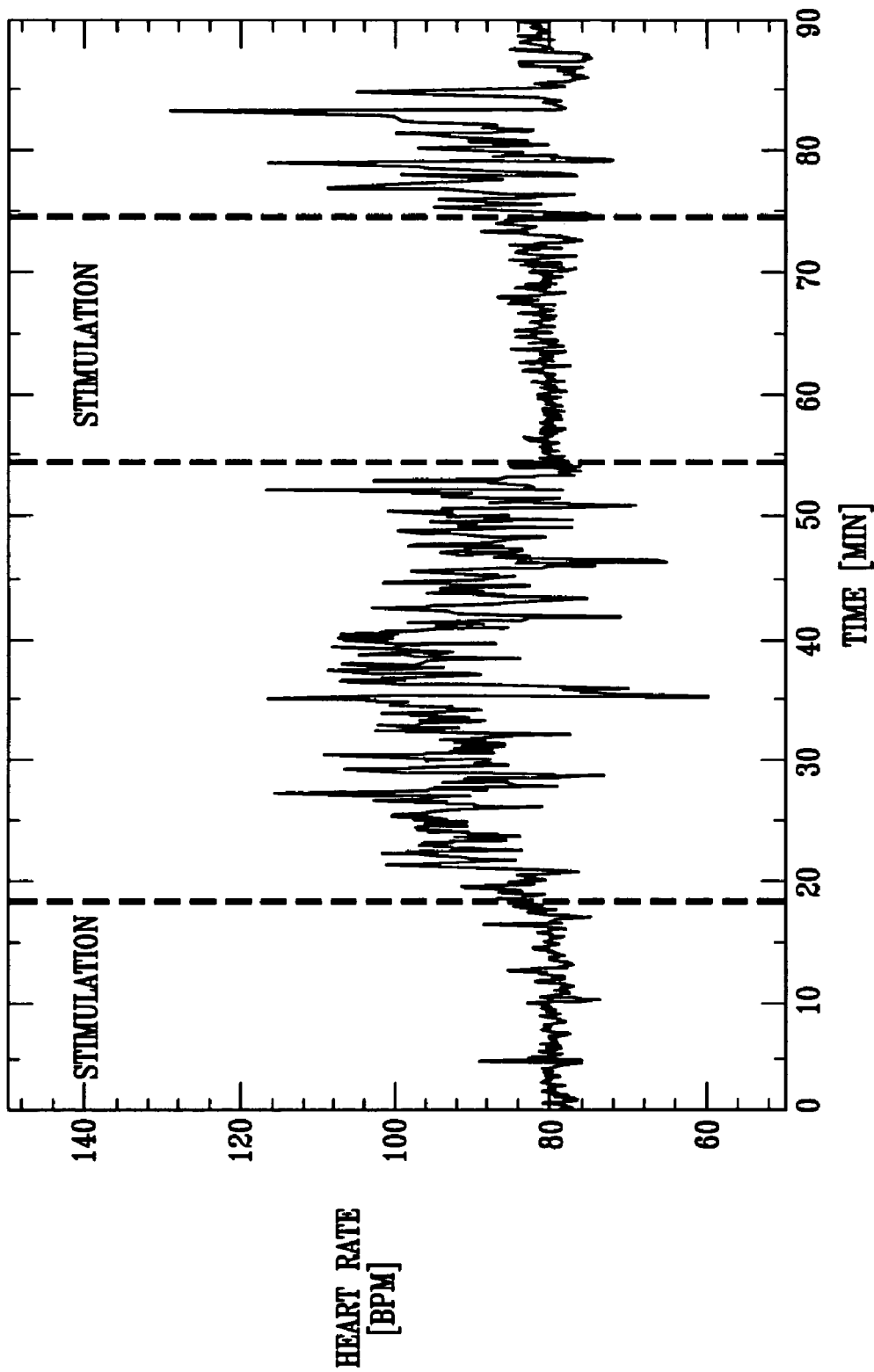
FIG. 6 is a graph showing in vivo experimental results, measured in accordance with an embodiment of the present invention.
Figure 10:
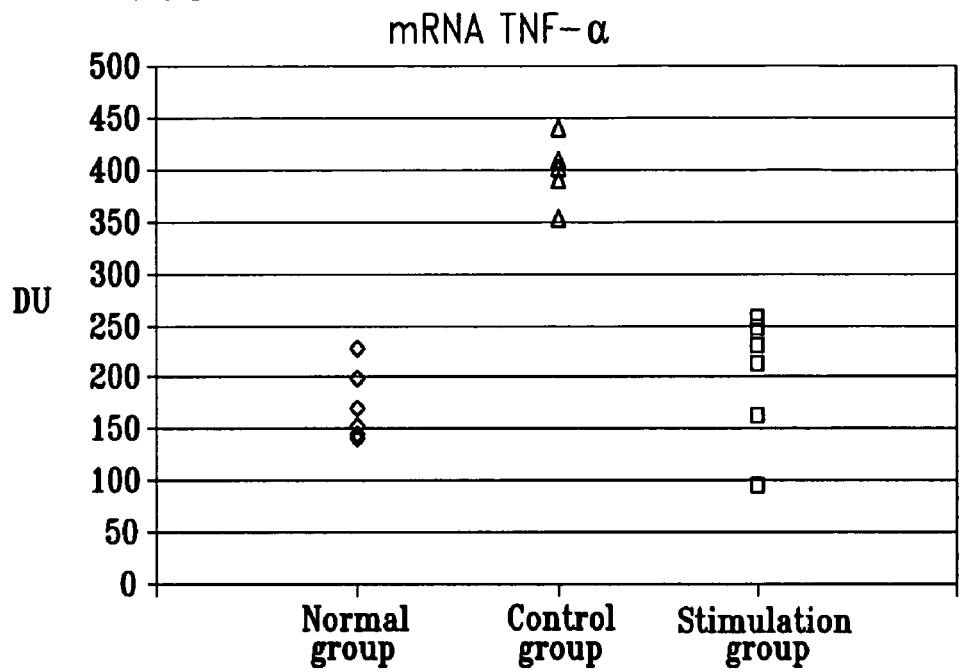
FIGS. 10-13 are graphs showing densitometry measurements of mRNA expression for TNF-alpha, IL-6, Activin-A, and TGF-beta, respectively, made during the experiment of FIGS. 7 and 8, measured in accordance with an embodiment of the present invention.
Figure 11:
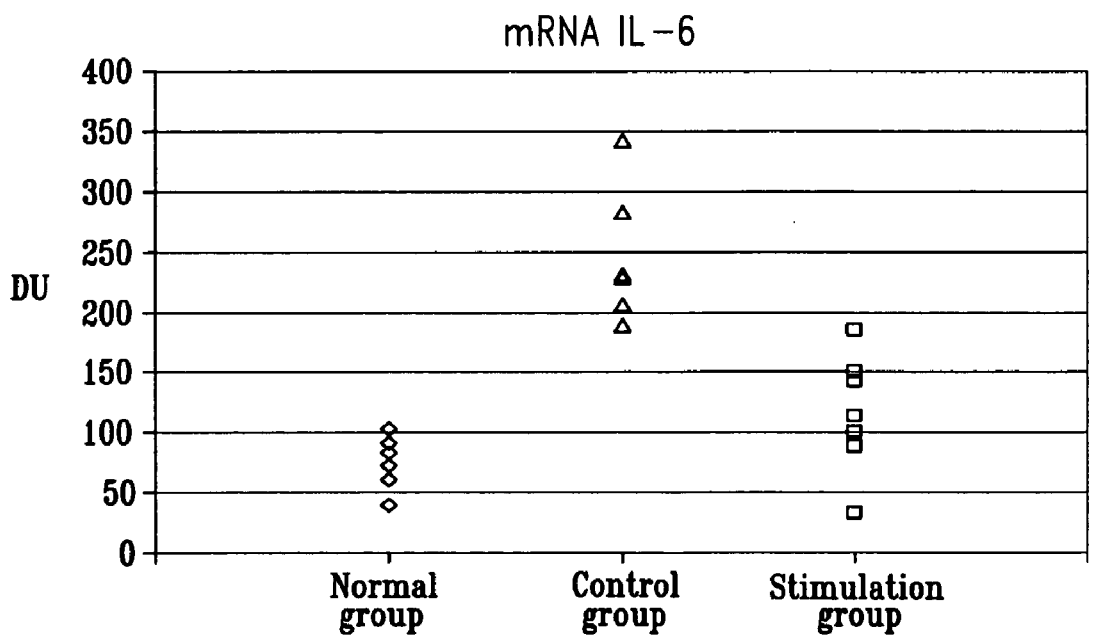
Figure 12:
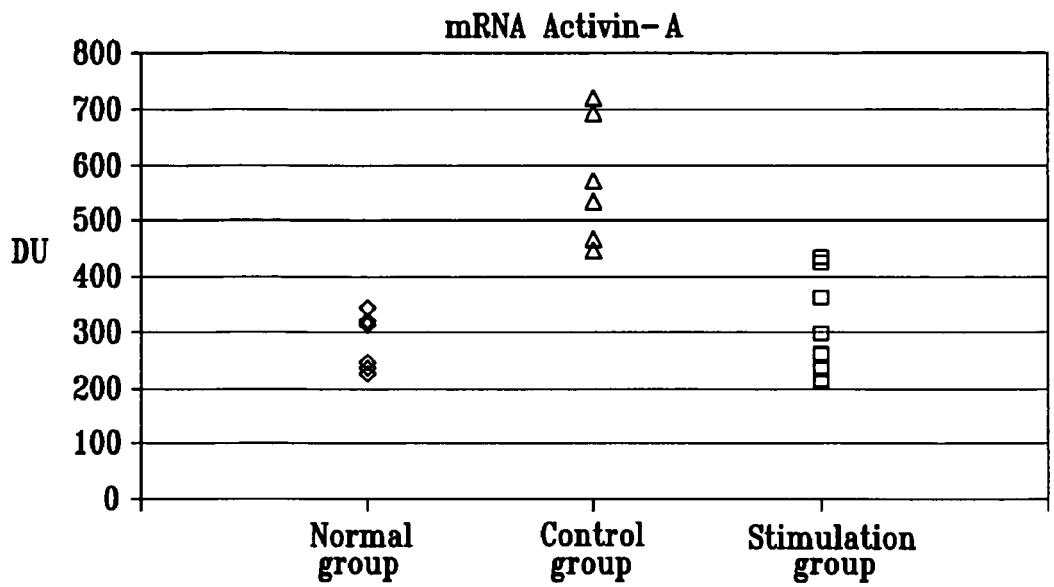
Figure 13:
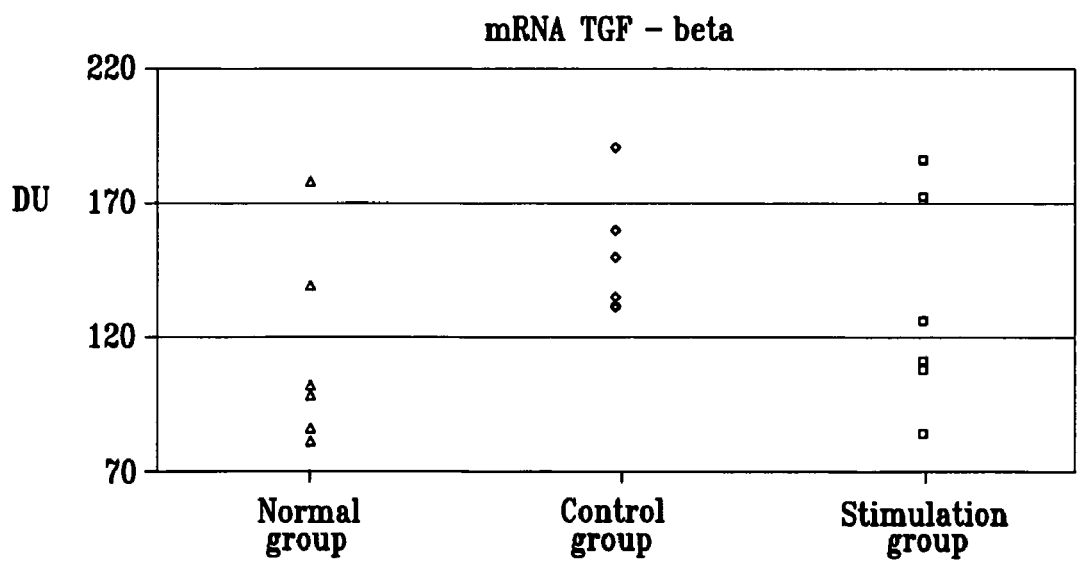

Reference is now made to FIG. 6, which is a graph showing in vivo experimental results, measured in accordance with an embodiment of the present invention. A dog was anesthetized, and cuff electrodes, similar to those described hereinabove with reference to FIG. 2B, were implanted in the right cervical vagus nerve. After a recovery period of two weeks, experimental vagal stimulation was applied to the dog while the dog was awake and allowed to move freely within its cage.

A control unit, similar to control unit 20, was programmed to apply vagal stimulation in a series of pulses, having the following parameters:

Stimulation synchronized with the intracardiac R-wave signal, with a delay from the R-wave of 60 ms;

Stimulation amplitude of 8 mA;

Stimulation pulse duration of 1 ms; and

Time between pulses within a burst of 5 ms.

The control unit implemented an integral feedback controller, similar to the integral feedback controller described hereinabove, in order to vary the number of pulses within a burst. The integral feedback controller used a target heart rate of 80 beats per minute. After 2 minutes of stimulation, the number of pulses within each burst was typically between about 1 and about 8.

During a first period and a third period from 0 to 18 minutes and 54 to 74 minutes, respectively, the control unit applied stimulation to the vagus nerve. Heart rate variability was substantially reduced, while an average heart rate of 80 beats per minute was maintained. (Baseline heart rate, without stimulation, was approximately 95 beats per minute.) During a second period and a fourth period from 18 to 54 minutes and 74 to 90 minutes, respectively, stimulation was discontinued, and, as a result, heart rate variability increased substantially, returning to normal values. Average heart rate during these non-stimulation periods increased to approximately 95 beats per minute (approximately baseline value). Thus, these experimental results demonstrate that the application of vagal stimulation using some of the techniques described herein results in a substantial reduction in heart rate variability.

Reference is made to FIGS. 7-15, which are graphs showing in vivo experimental results, measured in accordance with respective embodiments of the present invention. The objective of the study was to assess the efficacy of chronic vagus nerve stimulation therapy, using techniques described herein, in dogs with advanced chronic heart failure. Chronic heart failure was produced by multiple sequential intracoronary microembolizations.

A total of 19 healthy, conditioned purpose-bred mongrel dogs were entered into the study. Six of the dogs served as a non-sham-operated "normal" control group. These dogs, which underwent neither surgical implantations nor induced heart failure, were used in several of the analyses described hereinbelow with reference to FIGS. 9-15. The remaining 13 dogs underwent multiple sequential intracoronary microembolizations in order to produce chronic compensated heart failure (see the above-referenced articles by Sabbah H N et al. (1991 and 1994)). Embolizations were performed during cardiac catheterizations and were discontinued when left ventricular (LV) ejection fraction, determined angiographically, was approximately 35%. Cardiac catheterizations were preformed under general anesthesia and in sterile conditions. Anesthesia was induced using a combination of intravenous injections of hydromorphone (0.22 mg/kg) and diazepam (0.2-0.6 mg/kg), and a plane of anesthesia was maintained throughout the procedure with 1% to 2% isoflurane. During cardiac catheterizations, dogs were intubated and ventilated with room air.

Following the third coronary embolization and before the target ejection was reached, the 13 dogs were implanted with a system similar to vagal stimulation system 18, described hereinabove with reference to FIG. 1. The system comprised a control unit, which was implanted in the neck; a tripolar cuff electrode, which was positioned around the mid-right cervical vagus nerve; and an intracardiac electrode, which was positioned in the right ventricle and used for ECG and heart rate monitoring. An anterior longitudinal cervical incision was made at the midclavicular line. The right carotid sheath and right vagus nerve were exposed. The stimulation electrode was then placed around the vagus nerve and secured by tightening pre-existing tightening strings. A bend and a loop were created to avoid tension on the electrode due to head and neck movements. At least two more sutures were used to secure the electrode to the adjacent fascia. An active fixation ventricular lead was introduced into the right jugular vein and placed in the right ventricle apex using fluoroscopy. A subcutaneous tunnel between the cervical operational wound and the left side of the neck was made with a tunneling tool. The electrode wires and lead were passed through the tunnel and connected to the implantable generator placed in a previously created pocket on the left side of the neck.

A standard pacemaker unipolar ventricular electrode was used for sensing an intracardiac electrocardiogram. A tripolar vagus nerve cuff electrode was used, similar to that described with reference to FIG. 2B. The stimulation lead was connected to the nerve stimulator via two IS-1-like connectors. Adjustments were made while a programming wand was placed over the implanted nerve stimulator.

Two weeks after the last embolization (i.e., after the target ejection fraction was achieved), the 13 dogs underwent a left and right heart catheterization to evaluate LV function. The electrostimulation system was activated in 7 dogs. In the remaining 6 dogs, the system was not activated, such that these dogs served as a concurrent sham-operated placebo control group. In the control group the generators were implanted, but not activated.

The electrostimulation system was configured to adjust the impulse rate and intensity to keep the heart rate within a desired range. The control unit was programmed to apply vagal stimulation in a series of pulses, controlling the heart rate with the feedback algorithm described hereinabove, using the following parameters:

stimulation synchronized with the intracardiac R-wave signal, with a delay from detection of the R-wave of 100 ms;
stimulation current in the range of 4 to 8 mA;
stimulation pulse width of 1 ms;
each stimulation burst included between 0 and 8 pulses;
time between pulses within a burst of 5 ms; and
target heart rate was between 0 and 30 beats per minute above average heart rate.

All dogs were followed for 3 months. Hemodynamic, angiographic, echocardiographic, and electrocardiographic studies were performed just prior to activation of the system, and were repeated at the end of the 3 months of follow-up. After completing the final cardiac catheterization, and while under general anesthesia, the chest and abdomen were opened and examined for evidence of pleural effusion, pericardial effusion, and ascites. The heart was removed and LV tissue was prepared for histological and biochemical examination. Tissue samples were also obtained from lung, kidney, skeletal muscle, major blood vessels, and liver, and stored at −70° C. for future evaluation. Blood samples were collected at all study time points, and plasma samples were stored in cryotubes at −20° C. for future evaluation.

The primary endpoints of the study were:
prevention or attenuation of progressive LV dysfunction assessed by angiographic LV ejection fraction; and
prevention or attenuation of progressive LV remodeling assessed by measurements of LV end diastolic volume, LV end systolic volume, and LV chamber shape (sphericity), also determined from LV angiographic silhouettes.

The secondary endpoints of the study were:
prevention or attenuation of progressive LV diastolic dysfunction assessed by measuring: (1) LV peak −dP/dt, (2) LV deceleration time, (3) mitral valve velocity PE/PA ratio, and (4) LV end-diastolic circumferential wall stress;
extent of attenuation of cardiomyocyte hypertrophy, volume fraction of replacement fibrosis, and volume fraction of interstitial fibrosis;
capillary density and oxygen diffusion distance;
LV end-diastolic pressure determined by catheterization; and
presence and severity of functional mitral regurgitation.

All hemodynamic measurements were performed during cardiac catheterizations in anesthetized dogs. Measurements were made: (a) at baseline, prior to any embolizations (referred to as "baseline" hereinbelow), (b) at two weeks after the last embolization and prior to activation of the stimulation system and initiation of follow-up (referred to as "pre-treatment" hereinbelow), and (c) at 3 months after the initiation of therapy (referred to as "post-treatment" hereinbelow). The following parameters were evaluated in all dogs at all three study time periods: (1) aortic and LV pressures using catheter tip micromanometers (Millar Instruments), (2) peak rate of change of LV pressure during isovolumic contraction (peak +dP/dt) and relaxation (peak −dP/dt), and (3) LV end-diastolic pressure.

Left ventriculograms were performed during cardiac catheterization after completion of the hemodynamic measurements. Ventriculograms were performed with the dog placed on its right side, and were recorded on 35 mm cine at 30 frames/sec during a power injection of 15-20 ml of contrast material (RENO M 60, Squibb Diagnostics). Correction for image magnification was made using a radiopaque grid placed at the level of the LV. LV end-systolic (ESV) and end-diastolic (EDV) volumes were calculated from angiographic silhouettes using the area-length method (see the above-mentioned article by Dodge H T et al.). Premature beats and postextrasystolic beats were excluded from the analysis. LV ejection fraction was calculated as 100*(EDV−ESV)/EDV. Stroke volume was calculated as the difference between LV EDV and ESV, and cardiac output was calculated as the product of stroke volume and heart rate.

Global LV shape, a measure of LV sphericity, was quantified from angiographic silhouettes based upon the ratio of the major to minor axis at end-systole and end-diastole (see the above-mentioned article by Sabbah H N et al. (1992)). The major axis was drawn from the apex of the LV to the midpoint of the plane of the aortic valve. The minor axis was drawn perpendicular to the major axis at its midpoint. As this ratio decreases (i.e., approaches unity), the shape of the LV chamber approaches that of a sphere.

Echocardiographic and Doppler studies were performed in all dogs at all specified study time points, using a 77030A ultrasound system (Hewlett Packard) with a 3.5 MHZ transducer. All echocardiographic measurements were made with the dog placed in the right lateral decubitus position and recorded on a Panasonic 6300 VHS recorder for subsequent off-line analysis. LV fractional area shortening (FAS), a measure of LV systolic function, was measured from the short axis view at the level of the papillary muscles. LV thickness of the posterior wall and interventricular septum were measured, summed and divided by 2 to arrive at average LV wall thickness (h) to be used for calculating wall stress. LV major and minor semiaxes were measured and used for calculation of LV end-diastolic circumferential wall stress. Wall stress was calculated as described in Grossman W., *Cardiac Catheterization and Angiography,* 3rd ed., Philadelphia, Pa.: Lea & Febiger (1986), which is incorporated herein by reference, on p. 293.

Mitral inflow velocity was measured by pulsed-wave Doppler echocardiography. The velocity waveforms were used to calculate: (1) peak mitral flow velocity in early diastole (PE), peak mitral inflow velocity during LA contraction (PA), (3) the ratio of PE to PA, and (4) a deceleration time (DT) of the early rapid mitral inflow velocity waveform, a measure of LV relaxation. The presence or absence of functional mitral regurgitation (MR) was determined with Doppler color flow mapping (Hewlett Packard model 77020A Ultrasound System) using both apical two chamber and apical four chamber views. When present, the severity of functional MR was quantified based on the ratio of the regurgitant jet area to the area of the left atrium times 100. The ratios calculated from both views were then averaged to obtain a single representative measure of the severity of functional MR.

At the end of the protocol, after completion of all hemodynamic and angiographic studies, the chest and abdomen of the dogs were opened and examined grossly, as described above. Once the gross examination was completed, the heart was rapidly removed and placed in ice cold Tris Buffer (pH 7.4). Three 2 mm thick transverse slices were obtained from the LV (one from the basal third, one from the middle third, and one from the apical third), and were placed in 10% formalin. Transmural blocks were also obtained and rapidly frozen in isopentane cooled to −160° C. by liquid nitrogen, and stored at −70° C. until needed.

Formalin-fixed LV tissue slices were cut into smaller blocks (approximately 6). Each block was labeled for anatomical site, and embedded in paraffin blocks. Five micron thick sections were prepared and stained with Masson trichrome for quantification of replacement fibrosis. The extent of replacement fibrosis was calculated as the percent total surface area occupied by fibrous tissue. This measurement was made for each LV slice. The percent replacement fibrosis for each LV section was calculated as the average of all three slices (basal, middle, and apical). To quantify interstitial fibrosis, sections were stained with lectin. The volume fraction of interstitial collagen in regions remote from any infarcts were quantified as the percent total area occupied by collagen. For this morphometric analysis, 10 microscopic fields were selected at random from noninfarcted regions of each of 6 blocks. The overall volume fraction of interstitial collagen was calculated as the average value of all LV regions combined. Cardiomyocyte cross-sectional area, a measure of cardiomyocyte hypertrophy, was assessed from sections stained with lectin to delineate the myocyte border. Ten radially-oriented, scar free, microscopic fields (×40) were selected at random from each section and used to measure myocyte cross-sectional area by computer-assisted planimetry. Capillary density was measured also in sections stained with lectin-I. Capillary density was calculated as the number of capillaries per square millimeter and as the index capillary per fiber ratio (C/F). Oxygen diffusion distance was calculated as half the distance between two adjoining capillaries. For histological studies, LV tissue from the six dogs of the normal group was used.

Intragroup comparisons of hemodynamic, angiographic, echocardiographic, and Doppler variables within each of the two study groups were made between measurements obtained just before initiation of therapy and measurements made after completion of 3 months of therapy. For these comparisons, a Student's paired t-test was used, and a probability value <0.05 was considered significant. Study measurements were tested at baseline before any embolizations and at the time of assignment to study arms before initiation of therapy. Intergroup comparisons were made using a t-statistic for two means.

As can be seen in FIG. 7, there were no significant differences at baseline between the stimulation and control groups with respect to any of the hemodynamic, angiographic, echocardiographic and Doppler measurements. The p-values shown in this table are for the control group vs. the stimulation group. (The following abbreviations are used in the table: LV=left ventricular; AoP=aortic pressure; EDP=end-diastolic pressure; EDV=end-diastolic volume; ESV=end-systolic volume; EDSI=end-diastolic sphericity index; ESSI=end-systolic sphericity index; FAS=fractional area of shortening; and WS=wall stress.)

Similarly, as can be seen in FIG. 8, there were no significant differences between the two groups at pre-treatment except for mean aortic pressure, which was modestly but significantly lower in the control group than in the stimulation group. (The following abbreviations are used in the table: LV=left ventricular; AoP=aortic pressure; EDP=end-diastolic pressure; EDV=end-diastolic volume; ESV=end-systolic volume; EDSI=end-diastolic sphericity index; ESSI=end-systolic sphericity index; FAS=fractional area of shortening; WS=wall stress; and MR=functional mitral regurgitation.)

There were no differences between pre-treatment and post-treatment in the sham-operated control group with respect to heart rate, LV end-diastolic pressure, LV peak +dP/dt, LV peak −dP/dt, cardiac output, stroke volume, PE/PA ratio, DT, wall stress, or severity of functional MR. In the control group, however, there was a significant increase in mean aortic pressure, LV end-diastolic volume, and LV end-systolic volume. This was accompanied by a significant decline in LV ejection fraction and FAS. At the same time, ventricular sphericity increased, as evidenced by a significant reduction in LV end-systolic and end-diastolic major-to minor axis ratios, and by a significant increase in LV wall stress.

In the post-treatment analysis, comparisons were made between the sham-operated control group and the stimulation group, as shown in FIG. 8. Treatment with the stimulation system had no effect on heart rate or mean aortic pressure or on LV peak +dP/dt and peak −dP/dt. Treatment with the stimulation system did, however, significantly increase LV ejection fraction, LV FAS, cardiac output, stroke volume, sphericity indices, PE/PA ratio, and DT, while significantly decreasing LV end-diastolic pressure, EDV, ESV wall stress, and functional MR.

FIG. 9 shows the histomorphometric measurements from the six dogs of the normal group, the heart failure sham-operated dogs, and the heart failure dogs treated with the stimulation system. (In the table, VF=Volume Fraction.) Chronic stimulation using the stimulation system was associated with a significant reduction of volume fraction of replacement and interstitial fibrosis, a significant increase in capillary density, a significant decrease in myocyte cross-sectional area (a measure of myocyte hypertrophy), and a significant decrease in oxygen diffusion distance.

The results of this study indicate that chronic (3-month) therapy with the stimulation system in dogs with heart failure improves LV systolic and diastolic function. The improvement in systolic function is evidenced by increased LV ejection fraction, FAS, and stroke volume. The improvement in diastolic function is evidenced by reductions in LV preload, an increase in PE/PA ratio and DT, and a decrease in end-diastolic wall stress. At the global level, chronic therapy attenuated progressive LV remodeling, as evidenced by decreased LV chamber sphericity as well as LV size. At the cellular level, chronic therapy with the stimulation system attenuated remodeling, as evidenced by reduction of replacement and interstitial fibrosis, enhancing capillary density, shortening oxygen diffusion distance, and a decrease in myocyte hypertrophy.

LV tissue from all 13 dogs of the sham-operated control group and stimulation group, and from the six dogs of the normal group, was used to extract RNA. mRNA expression for TNF-alpha, IL-6, Activin-A, and TGF-beta was measured using reverse transcriptase polymerase chain reaction (RT-PCR), and the bands obtained after gel electrophoresis were quantified in densitometric units (du). As can be seen in FIGS. 10-13, mRNA expression for all four cytokines was significantly higher in the sham-control group than in the normal group, and vagal stimulation therapy reduced mRNA expression of all four cytokines in the stimulation group compared to the sham-control group.

Figure 14A:
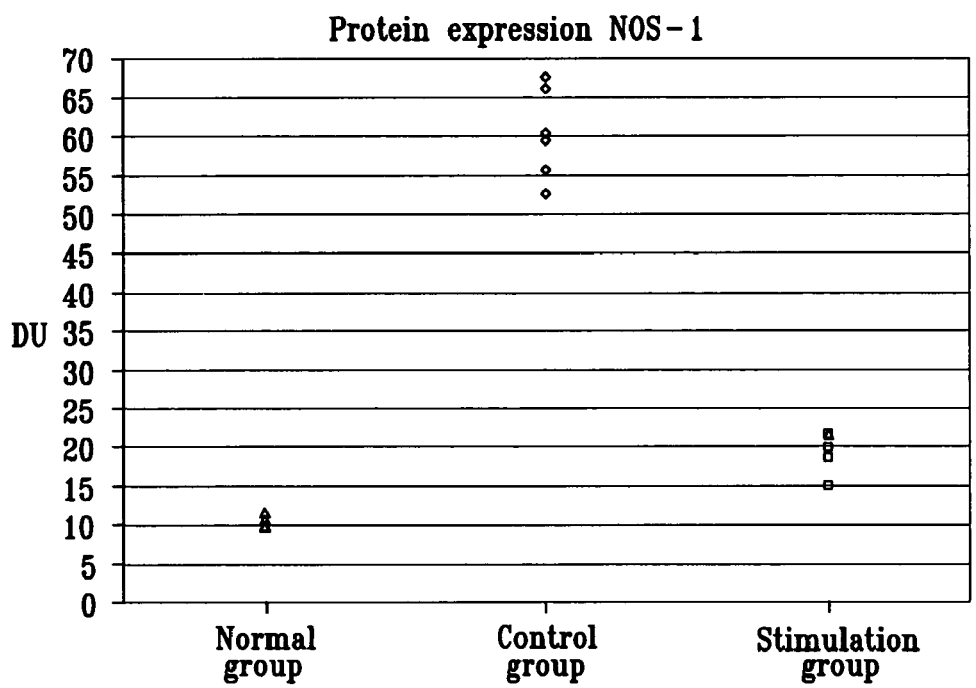
FIGS. 14A, 14B, and 14C are graphs showing densitometry measurements of protein expression of NOS-1, NOS-2, and NOS-3, respectively, made during the experiment of FIGS. 7 and 8, measured in accordance with an embodiment of the present invention.
Figure 14B:
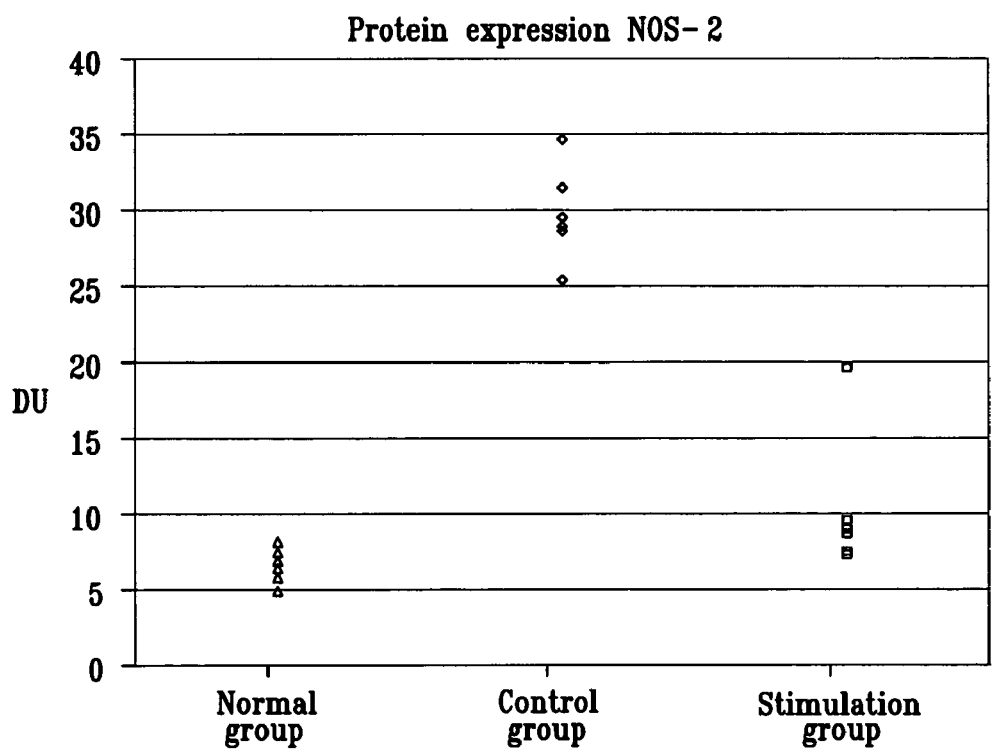
Figure 14C:
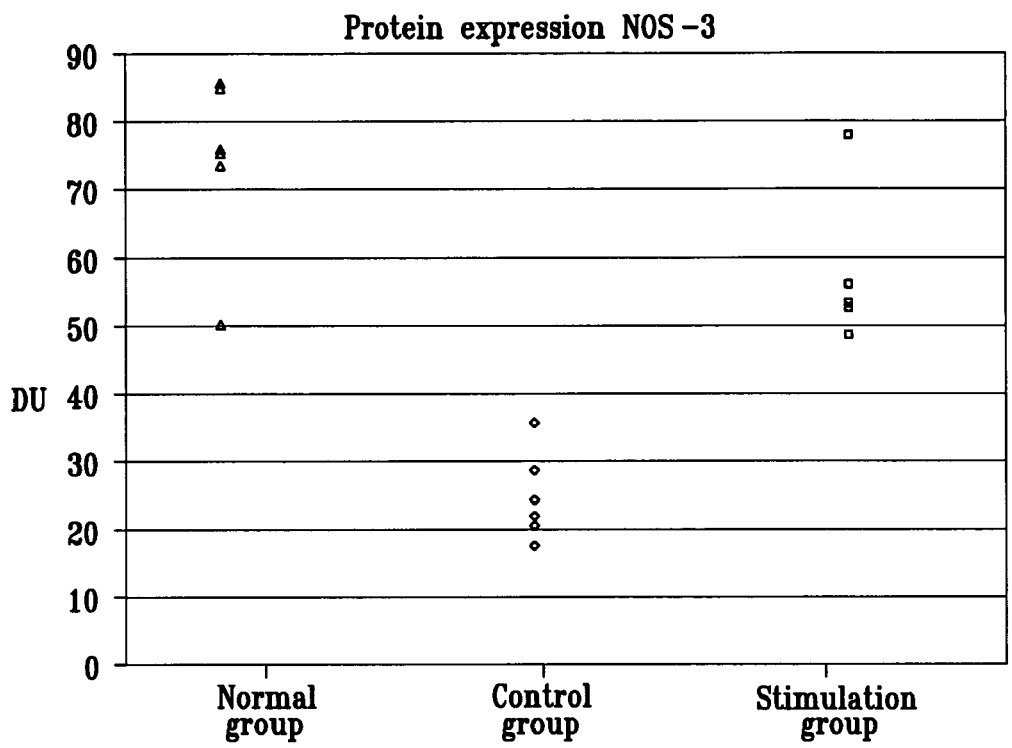

FIGS. 14A, 14B, and 14C are graphs showing the levels of protein expression of NOS-1, NOS-2, and NOS-3, respectively, in each dog of the normal group, the heart failure sham-operated group, and the stimulation group treated with the stimulation system. Protein expression was measured in tissue homogenate using Western blots, and the bands were quantified in densitometric units (du).

As can be seen in FIGS. 14A-C, protein expression of NOS-3 decreased, and NOS-1 and NOS-2 were significantly higher in the sham-operated control group than in the normal group. Three months' treatment with the stimulation system statistically significantly reduced mRNA and protein expression of NOS-1 and NOS-2, and statistically significantly increased mRNA and protein expression of NOS-3, thereby normalizing mRNA and protein expression of NOS-1, NOS-2, and NOS-3. The inventors believe that such normalization of mRNA and protein expression of NOS-1, NOS-2, and NOS-3 in LV myocardium explains, in part, the improvement in global LV function observed when dogs with heart failure received long-term treatment with the electrical stimulation therapy described herein. In an embodiment of the present invention, vagal stimulation applied using techniques described herein is configured to reduce expression of NOS-1 and/or NOS-2, and/or to increase expression of NOS-3.

Figure 15:
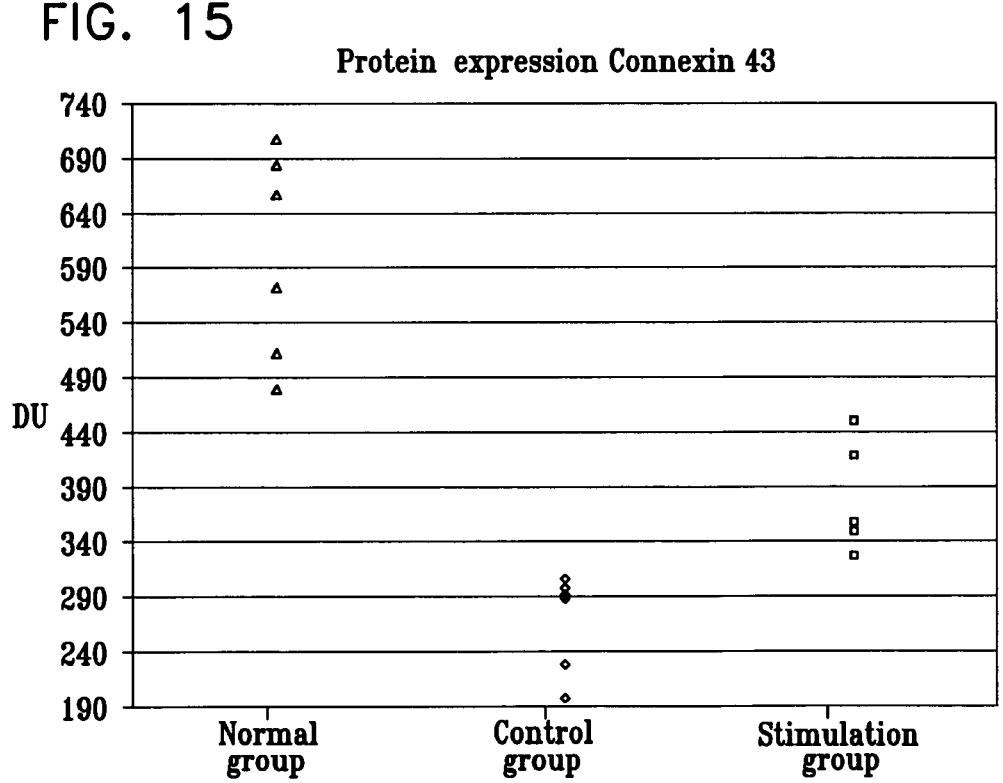
FIG. 15 is a graph showing densitometry measurements of protein expression of Connexin 43, made during the experiment of FIGS. 7 and 8, measured in accordance with an embodiment of the present invention.

FIG. 15 is a graph showing the densitometry levels of Connexin 43 in LV tissue of each dog of the normal group, the heart failure sham-operated group, and the stimulation group treated with the stimulation system. As can be seen in the graph, stimulation with the system caused a statistically significant increase in levels of Connexin 43 protein. The ventricular Connexin 43 protein level is substantially reduced in ischemia and heart failure. In a mouse model, reduced expression of Connexin 43 increases the incidence of ventricular tachyarrhythmias and causes a significant reduction in conduction velocity. These results suggest that reduction of Connexin 43 in ventricular tissue promotes conditions such as heart failure. In an embodiment of the present invention, vagal stimulation applied using techniques described herein is configured to increase Connexin 43 levels sufficiently to treat a cardiac condition of the subject, such as heart failure.

Figure 16:
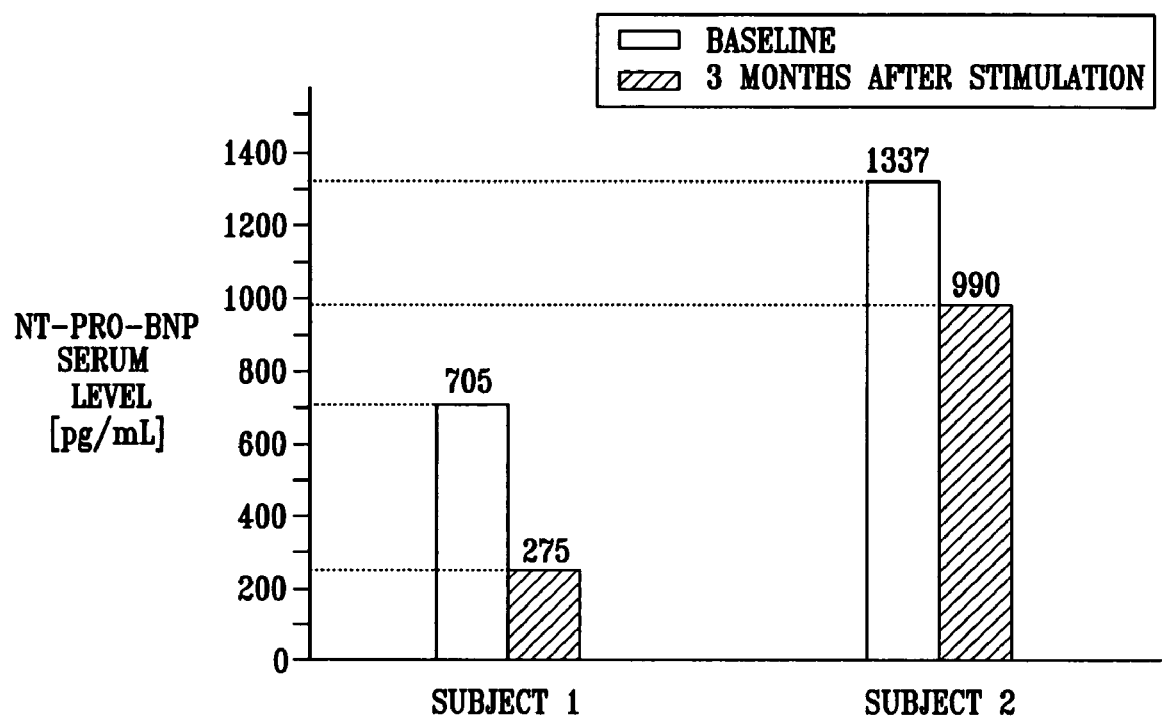
FIG. 16 is a graph showing N-terminal pro-brain natriuretic peptide (NT-pro-BNP) serum levels in two human subjects, measured in accordance with an embodiment of the present invention.

FIG. 16 is a graph showing N-terminal pro-brain natriuretic peptide (NT-pro-BNP) serum levels in two human subjects, measured in accordance with an embodiment of the present invention. Two human heart failure subjects (NYHA class III) were implanted, under general anesthesia, with a system similar to vagal stimulation system 18, described hereinabove with reference to FIG. 1. The system comprised a control unit, which was implanted in the subject's chest; a tripolar cuff electrode, which was positioned around the mid-right cervical vagus nerve; and an intracardiac electrode, which was positioned in the right ventricle and used for ECG and heart rate monitoring. The control unit was programmed to apply vagal stimulation in a series of pulses, having the following parameters:

stimulation synchronized with the intracardiac R-wave signal, with a delay from detection of the R-wave of 100 ms;
stimulation current in the range of 2 to 4 mA;
stimulation pulse width of 1 ms;
each stimulation burst included between 0 and 3 pulses; and
time between pulses within a burst of 5 ms.

The stimulation system was activated two weeks after implantation. Blood samples were taken before activation (baseline) and three months after activation. NT-pro-BNP serum levels, a standard diagnostic indicator of the severity of heart failure, were measured using a standard ELISA procedure. As can be seen in the graph, the NT-pro-BNP levels decreased in one subject from 705 to 275, and in a second subject from 1337 to 990. These results demonstrate that vagal stimulation using techniques described herein resulted in improved cardiac function in two human subjects.

In an embodiment of the present invention, vagal stimulation performed using the techniques described herein affects one or more of the following physiological parameters:

Hemodynamic and Cardiac Geometry Parameters
mean aortic pressure (mmHg)
left ventricular end-diastolic pressure (mmHg)
peak +dP/dt (mmHg/sec)
peak −dP/dt (mmHg/sec)
cardiac output (L/min)
stroke volume (ml)
left ventricular end-diastolic volume (ml)
left ventricular end-systolic volume (ml)

left ventricular Ejection Fraction (%)
left ventricular end-diastolic sphericity index
left ventricular end-systolic sphericity index
left ventricular fractional area of shortening (%)
ratio of peak mitral flow velocity in early diastole (PE) to peak mitral inflow velocity during left atrial contraction (PA)
deceleration time of the early rapid mitral inflow velocity waveform (msec)
left ventricular end-diastolic circumferential wall stress (gm/cm2)
severity of mitral regurgitation (%)
systemic vascular resistance
pulmonary vascular resistance
coronary blood flow
vagal tone
heart rate variability
baroreceptor sensitivity
pulmonary residual volumes and pressures (which facilitate gas exchange and prevent pulmonary edema)
VO2 Max
intracardiac conduction
AV delay
atrial contractility (improvements of which cause less backflow into the lungs, less stress on the myocardium, smaller ventricular volumes and reduced volume overload on the LV)

Myocardial Cellular Anatomy Parameters
volume fraction replacement fibrosis (%)
volume fraction interstitial fibrosis (%)
capillary density (cap/mm2)
capillary/fiber ratio
oxygen diffusion distance (μm)
myocyte cross-sectional area (μm2)
apoptosis
level of homogeneity of the myocardium
activation of alpha-adrenergic receptors.

Inflammatory Markers
tumor necrosis factor alpha
interleukin 6
activin A
transforming growth factor
interferon
interleukin 1 beta
interleukin 18
interleukin 12
C-reactive protein Neurohormone Peptide
brain natriuretic peptide (BNP), e.g., N-terminal pro-BNP (NT-pro-BNP)
a catecholamine NO Synthases (NOSs)
neural NOS (nNOS, or NOS-1)
inducible NOS (iNOS, or NOS-2)
endothelial NOS (eNOS, or NOS-3)

Gap Junction Proteins
Connexin, e.g., Connexin 43

In an embodiment of the present invention, vagal stimulation is performed using the techniques described herein to treat one or more of the following cardiac pathologies: heart failure, congestive heart failure, diastolic heart failure, atrial fibrillation, atherosclerosis, restenosis, myocarditis, cardiomyopathy, myocardial infarction, post-myocardial infarct remodeling, angina, hypertension, arrhythmia, endocarditis, arteritis, thrombophlebitis, pericarditis, myocardial ischemia, sick sinus syndrome, cardiogenic shock, and cardiac arrest.

In an embodiment of the present invention, vagal stimulation is performed using the techniques described herein to treat a "stimulation-treatable condition." A "stimulation-treatable condition," as used in the present application, including in the claims, means a condition selected from the list consisting of: meningitis, encephalitis, multiple sclerosis, cerebral infarction, a cerebral embolism, Guillaume-Barre syndrome, neuritis, neuralgia, spinal cord injury, paralysis, Alzheimer's disease, Parkinson's disease, depression, psychosis, schizophrenia, anxiety, autism, an attention disorder, trauma, spinal cord trauma, CNS trauma, a headache, a migraine headache, back pain, neck pain, syncope, faintness, dizziness, vertigo, memory loss, sleep disorders, insomnia, hypersomnia, dementia, glaucoma, appendicitis, a peptic ulcer, a gastric ulcer, a duodenal ulcer, peritonitis, pancreatitis, ulcerative colitis, pseudomembranous colitis, acute colitis, ischemic colitis, diverticulitis, epiglottitis, achalasia, cholangitis, cholecystitis, hepatitis, Crohn's disease, cirrhosis, inflammatory bowel disease (IBD), dysphagia, nausea, constipation, obesity, an eating disorder, gastrointestinal bleeding, acute renal failure, chronic renal failure, a glomerular disease, cystitis, incontinence, a urinary tract infection and pyelonephritis, enteritis, Whipple's disease, asthma, an allergy, anaphylactic shock, an immune complex disease, organ ischemia, a reperfusion injury, organ necrosis, hay fever, sepsis, septicemia, septic shock, cachexia, hyperpyrexia, eosinophilic granuloma, granulomatosis, sarcoidosis, septic abortion, epididymitis, vaginitis, prostatitis, eczema, urethritis, proteinuria, bronchitis, emphysema, rhinitis, cystic fibrosis, chronic obstructive pulmonary disease, sleep apnea, pneumonitis, pneumoultramicroscopicsilicovolcanoconiosis, alveolitis, bronchiolitis, an infection of the upper respiratory tract, pulmonary edema, edema, pharyngitis, pleurisy, sinusitis, influenza, respiratory syncytial virus infection, herpes infection, HIV infection, hepatitis B virus infection, hepatitis C virus infection, disseminated bacteremia, tuberculosis, an Epstein-Barr virus infection, Dengue fever, candidiasis, malaria, filariasis, amebiasis, a hydatid cyst, a burn, dermatitis, dermatomyositis, sunburn, urticaria, a wart, a wheal, periarteritis nodosa, rheumatic fever, coeliac disease, adult respiratory distress syndrome, uveitis, arthritides, arthralgias, osteomyelitis, fasciitis, Paget's disease, gout, periodontal disease, rheumatoid arthritis, synovitis, myasthenia gravis, thyroiditis, systemic lupus erythematosus, sarcoidosis, amyloidosis, osteoarthritis, fibromyalgia, chronic fatigue syndrome, Goodpasture's syndrome, Behcet's syndrome, Familial Mediterranean Fever, Sjogren syndrome, allograft rejection, graft-versus-host disease, Type I diabetes, Type II diabetes, ankylosing spondylitis, Berger's disease, sexual dysfunction, impotence, a neoplastic disorder, vasculitis, osteoporosis, a disorder of the pituitary, a disorder of the adrenal cortex, a seizure, epilepsy, an ataxic disorder, a prion disease, autism, a cerebrovascular disease, peripheral neuropathy, an addiction, an alcohol addiction, a nicotine addiction, a drug addiction, an autoimmune disease, a neurological disorder, pain, a psychiatric disorder, a skin disease, an infectious disease, a vascular disease, a kidney disorder, and a urinary tract disorder.

In an embodiment of the present invention, vagal stimulation is performed using the techniques described herein to treat one or more of the following organs or other portions of the body: a heart, a brain, lungs and/or other organs of the respiratory system, a liver, a kidney, a stomach, a small intestine, a large intestine, a muscle of a limb, a central nervous system, a peripheral nervous system, a pancreas, a bladder, skin, a urinary tract, a thyroid gland, a pituitary gland, and an adrenal cortex.

In an embodiment of the present invention, vagal stimulation using the techniques described herein attenuates muscle contractility.

In an embodiment of the present invention, vagal stimulation is performed using the techniques described herein to treat one or more of the following non-cardiac pathologies related to Connexin 43 (for each condition, an article cited hereinabove is indicated that describes the relationship between Connexin 43 and the condition): tuberous sclerosis (Mak B C et al.), breast cancer (Gould V E et al.), carcinoma (Gould V E et al.), melanoma (Haass N K et al.), osteoarthritis (Marino A A et al.), a wound (Brandner J M et al.), a seizure (Gajda Z et al.), bladder overactivity (Christ G J et al.), bladder outlet obstruction (Haefliger J A et al.), Huntington's disease (Vis J C et al.), and Alzheimer's disease (Nagy J I et al.).

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/064,446, filed Feb. 22, 2005, entitled, "Techniques for applying, configuring, and coordinating nerve fiber stimulation";

U.S. patent application Ser. No. 11/062,324, filed Feb. 18, 2005, entitled, "Techniques for applying, calibrating, and controlling nerve fiber stimulation";

U.S. patent application Ser. No. 10/719,659, filed Nov. 20, 2003, entitled, "Selective nerve fiber stimulation for treating heart conditions";

PCT Patent Application PCT/IL03/00431, filed May 23, 2003, entitled, "Selective nerve fiber stimulation for treating heart conditions";

PCT Patent Application PCT/IL03/00430, filed May 23, 2003, entitled, "Electrode assembly for nerve control";

U.S. patent application Ser. No. 10/205,475, filed Jul. 24, 2002, entitled, "Selective nerve fiber stimulation for treating heart conditions";

U.S. patent application Ser. No. 09/944,913, filed Aug. 31, 2001, entitled, "Treatment of disorders by unidirectional nerve stimulation," which issued as U.S. Pat. No. 6,684,105;

PCT Patent Application PCT/IL02/00068, filed Jan. 23, 2002, entitled, "Treatment of disorders by unidirectional nerve stimulation," and U.S. patent application Ser. No. 10/488,334 in the national stage thereof, filed Jul. 6, 2004;

U.S. Provisional Patent Application 60/383,157 to Ayal et al., filed May 23, 2002, entitled, "Inverse recruitment for autonomic nerve systems";

U.S. Provisional Patent Application 60/612,428, filed Sep. 23, 2004, entitled, "Inflammation reduction by vagal stimulation";

U.S. Provisional Patent Application 60/668,275, filed Apr. 4, 2005, entitled, "Parameter improvement by vagal stimulation";

U.S. patent application Ser. No. 11/022,011, filed Dec. 22, 2004, entitled, "Construction of electrode assembly for nerve control";

U.S. Provisional Patent Application 60/628,391, filed Nov. 15, 2004, entitled, "Electrode array for selective unidirectional stimulation";

U.S. patent application Ser. No. 10/461,696, filed Jun. 13, 2003, entitled, "Vagal stimulation for anti-embolic therapy";

U.S. Provisional Patent Application 60/478,576, filed Jun. 13, 2003, entitled, "Applications of vagal stimulation";

PCT Patent Application PCT/IL04/000496, filed Jun. 10, 2004, entitled, "Vagal stimulation for anti-embolic therapy";

PCT Patent Application PCT/IL04/000495, filed Jun. 10, 2004, entitled, "Applications of vagal stimulation";

U.S. Provisional Patent Application 60/655,604 to Ben-David et al., filed Feb. 22, 2005;

U.S. patent application Ser. No. 11/062,324, filed Feb. 18, 2005, entitled, "Techniques for applying, calibrating, and controlling nerve fiber stimulation";

U.S. patent application Ser. No. 11/064,446, filed Feb. 22, 2005, entitled, "Techniques for applying, configuring, and coordinating nerve fiber stimulation";

U.S. patent application Ser. No. 10/866,601, filed Jun. 10, 2004, entitled, "Applications of vagal stimulation"; and U.S. patent application Ser. No. 10/205,474, filed Jul. 24, 2002, entitled, "Electrode assembly for nerve control."

Although embodiments of the invention are generally described herein with respect to electrical transmission of power and electrical stimulation of tissue, other modes of stimulation may also be used, such as magnetic stimulation or chemical stimulation.

The techniques described herein may be performed in combination with other techniques, which are known in the art or which are described in the references cited herein, that stimulate an autonomic nerve, such as the vagus nerve, in order to achieve a desired therapeutic end.

For some applications, techniques described herein are used to apply controlled stimulation to one or more of the following: the lacrimal nerve, the salivary nerve, the vagus nerve, the pelvic splanchnic nerve, or one or more sympathetic or parasympathetic autonomic nerves. Such controlled stimulation may be used, for example, to regulate or treat a condition of the lung, heart, stomach, pancreas, small intestine, liver, spleen, kidney, bladder, rectum, large intestine, reproductive organs, or adrenal gland.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a condition of a subject, comprising:
   identifying the subject as suffering from heart failure;
   treating the heart failure by applying a stimulating current to parasympathetic nervous tissue of the subject, and configuring the stimulating current to change a level of protein expression of at least one NO synthase of the subject selected from the group consisting of: NOS-1, NOS-2, and NOS-3; and
   thereafter, measuring the level of the protein expression of the at least one NO synthase, and evaluating an effectiveness of the current application by assessing at least one change in the level of the protein expression of the at least one NO synthase, the change selected from the group consisting of: a reduction in the level of the protein expression of NOS-1, a reduction in the level of the protein expression of NOS-2, and an increase in the level of the protein expression of NOS-3.

2. The method according to claim 1, wherein configuring the stimulating current comprises configuring the stimulating current to reduce the level of the protein expression of NOS-1 and the level of the protein expression of NOS-2, and to increase the level of the protein expression of NOS-3.

3. The method according to claim 1, wherein applying the stimulating current comprises applying the stimulating current during a period having a duration of at least one week.

4. The method according to claim 1, wherein configuring the stimulating current comprises configuring the stimulating current to change the level of the protein expression of the at least one NO synthase of heart tissue of the subject.

5. The method according to claim 1, wherein the parasympathetic tissue includes a vagus nerve of the subject, and wherein applying the stimulating current comprises applying the stimulating current to the vagus nerve.

6. The method according to claim 1, wherein the parasympathetic tissue includes an epicardial fat pad of the subject, and wherein applying the stimulating current comprises applying the stimulating current to the epicardial fat pad.

7. The method according to claim 1, wherein the parasympathetic tissue is selected from the group consisting of: parasympathetic tissue of a pulmonary vein, parasympathetic tissue of a carotid artery, parasympathetic tissue of a carotid sinus, parasympathetic tissue of a coronary sinus, parasympathetic tissue of a vena cava vein, parasympathetic tissue of a right ventricle, and parasympathetic tissue of a jugular vein, and wherein applying the stimulating current comprises applying the stimulating current to the selected parasympathetic tissue.

8. The method according to claim 1, wherein measuring the level of the protein expression of the at least one NO synthase comprises quantifying the level of the protein expression in densitometric units (du).

9. The method according to claim 8, wherein measuring the level of the protein expression comprises measuring the level of the protein expression of the at least one NO synthase in myocardium of the subject.

10. The method according to claim 5, wherein configuring the stimulating current comprises delivering the stimulating current in a series of bursts that commence in respective cardiac cycles after a delay after a feature of an electrocardiogram (ECG), each of which bursts includes up to 8 pulses having a pulse repetition interval of greater than 3 ms, and each of which pulses has a duration of between 0.2 and 4 ms, and an amplitude of between 2 and 10 mA.

11. The method according to claim 10, wherein configuring the stimulating current comprises commencing the bursts in the respective cardiac cycles after a delay from detection of an R-wave.

12. The method according to claim 10, wherein configuring the stimulating current comprises setting the amplitude to between 4 and 8 mA.

13. The method according to claim 10, wherein configuring the stimulating current comprises setting the pulse width to 1 ms.

14. The method according to claim 10, wherein configuring the stimulating current comprises setting the pulse repetition interval to 5 ms.

15. The method according to claim 10, wherein configuring the stimulating current comprises commencing the bursts in the respective cardiac cycles after a delay from detection of an R-wave, setting the amplitude to between 4 and 8 mA, setting the pulse width to 1 ms, and setting the pulse repetition interval to 5 ms.

16. The method according to claim 1, wherein assessing comprises assessing the reduction in the level of the protein expression of NOS-1, the reduction in the level of the protein expression of NOS-2, and the increase in the level of the protein expression of NOS-3.

* * * * *